US007541173B2

(12) United States Patent
Bramucci et al.

(10) Patent No.: US 7,541,173 B2
(45) Date of Patent: Jun. 2, 2009

(54) SOLVENT TOLERANT MICROORGANISMS AND METHODS OF ISOLATION

(75) Inventors: Michael G. Bramucci, Boothwyn, PA (US); Vasantha Nagarajan, Wilmington, DE (US); Natalia Sedkova, Cherry Hill, NJ (US); Manjari Singh, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 23 days.

(21) Appl. No.: 11/761,497

(22) Filed: Jun. 12, 2007

(65) Prior Publication Data

US 2008/0124774 A1 May 29, 2008

Related U.S. Application Data

(60) Provisional application No. 60/813,779, filed on Jun. 15, 2006.

(51) Int. Cl.
*C12N 1/20* (2006.01)
*C12N 1/21* (2006.01)
*C12P 7/16* (2006.01)

(52) U.S. Cl. .................... 435/252.3; 435/148; 435/160; 435/252.2; 435/252.31; 435/252.34; 435/252.4; 435/252.9

(58) Field of Classification Search ....................... None
See application file for complete search history.

(56) References Cited

U.S. PATENT DOCUMENTS

| | | | | |
|---|---|---|---|---|
| 4,424,275 | A | 1/1984 | Levy | |
| 4,568,643 | A | 2/1986 | Levy | |
| 4,757,010 | A | 7/1988 | Hermann et al. | |
| 5,192,673 | A | 3/1993 | Jain et al. | |
| 5,210,032 | A | 5/1993 | Kashket | |
| 6,358,717 | B1 | 3/2002 | Blaschek et al. | |
| 6,960,465 | B1 | 11/2005 | Papoutsakis et al. | |
| 2002/0028492 | A1 | 3/2002 | Lenke et al. | |
| 2003/0162271 | A1 | 8/2003 | Zhang et al. | |
| 2007/0218533 | A1 | 9/2007 | Gill et al. | |
| 2007/0259410 | A1 | 11/2007 | Donaldson et al. | |
| 2007/0259411 | A1* | 11/2007 | Bramucci et al. | 435/160 |
| 2007/0292927 | A1* | 12/2007 | Donaldson et al. | 435/160 |

FOREIGN PATENT DOCUMENTS

| | | | |
|---|---|---|---|
| CA | 2039245 | | 3/1991 |
| EP | 0 112 459 | A1 | 7/1984 |
| EP | 0 282 474 | A1 | 9/1988 |
| EP | 0 315 949 | A1 | 5/1989 |
| EP | 1 149 918 | A1 | 4/2000 |
| JP | 61-209594 | | 9/1986 |
| JP | 63-017695 | | 4/1988 |
| JP | 63-102687 | | 5/1988 |
| JP | 63-254986 | | 10/1988 |
| WO | WO 90/02193 | A1 | 3/1990 |
| WO | WO 98/51813 | A1 | 11/1998 |
| WO | WO 2007/130518 | A2 | 11/2007 |

OTHER PUBLICATIONS

Underwood et al., Genetic Changes to Optimize Carbon Partitioning Between Ethanol and Biosynthesis in Ethanologenic *Escherichia coli*, Appl. Environ. Microbiol., 2002, vol. 68:6263-6272.

Fontaine et al., Molecular Characterization and Transcriptional Analysis of adhE2, the Gene Encoding the Nadh-Dependent Aldehyde/Alcohol Dehydrogenase Responsible for Butanol Production Alcohologenic Cultures of Clostridium Acetobutylicum ATCC 824, Journal of Bacteriology, 2002, vol. 184:821-830.

Cornillot et al., The Genes for Butanol and Acetone Formation in Clostridium Acetobutylicum ATCC 824 Reside on a Large Plasmid Whose Loss Leads to Degeneration of the Strain, Journal of Bacteriology, 1997, vol. 179:5442-5447.

Bermejo et al., Expression of Clostridium Acetobutylicum ATCC 824 Genes in *Escherichia coli* for Acetone Production and Acetate Detoxification, Applied and Environmental, 1998, vol. 64:1079-1085.

D.R. Woods, The Genetic Engineering of Microbial Solvent Production, Trends in Biotechnology, 1995, vol. 13:259-264.

P. Durre, New Insights and Novel Developments in Clostridial Acetone/Butanol/Isopropanol Fermentation, Applied Microbiology and Biotechnology, 1998, vol. 49:639-648.

Harris et al., Characterization of Recombinant Strains of the Clostridium Acetobutylicum Butyrate Kinase Inactivation Mutant: Needs for New Phenomenological Models for Solventogenesis and Butanol Inhibition?, Biotechnology and Bioengineering, 2000, vol. 67:1-11.

Speranza et al., Conversion of Meso-2,3-Butanediol into 2-Butanol by *Lactobacilli*. Stereochemical and Enzymatic Aspects, Journal of Argicultural and Food Chemistry Society, 1997, vol. 45:3476-3480.

Keen et al., The Formation of 2 Butanone and 2 Butanol in Cheddar Cheese, Journal of Dairy Research, 1974, vol. 41:249-257.

Matsumoto et al., Toxicity of Ionic Liquids and Organic Solvents to Lactic Acid-Producing Bacteria, Journal of Bioscience and Bioengineering, 2004, vol. 98:344-347.

Butanols, Ullmann's Encyclopedia of Industrial Chemistry, 6th Edition, 2003, vol. 5:716-719.

Carlini et al., Guerbet Condensation of Methanol with N-Propanol to Isobutyl Alcohol Over Heterogeneous Copper Chromite/Mg-A1 Mixed Oxides Catalysts, J. Molec. Catal. A: Chem., 2004, vol. 220:215-220.

Girbal et al., Regulation of Solvent Production in *Clostridium Acetobutylicum*, Trends in Biotechnology, 1998, vol. 16:11-16.

Tomas et al., Overexpression of groESL in *Clostridium Acetobutylicum* Results in Increased Solvent Production and Tolerence, Prolonged Metabolism, and Changes in the Cell's Transcriptional Program, Appl. Environ. Microbiol., 2003, vol. 69:4951-4965.

(Continued)

*Primary Examiner*—Herbert J. Lilling

(57) ABSTRACT

*Lactobacillus* bacteria having enhanced tolerance to butanols have been isolated. The bacteria are useful for the fermentive production of butanol. New methods for the isolation of butanol tolerant *Lactobacillus* are also provided.

28 Claims, No Drawings

OTHER PUBLICATIONS

Quratulain et al., Development and Characterization of Butanol-Resistant Strain of *Clostridium Acetobutylicum* in Molasses Medium, *Folia Microbiologica*, 1995, vol. 40:467-471.

Soucaille et al., Butanol Tolerance and Autobacteriocin Production by *Clostridium Acetobutylicum*, Current Microbiology, 1987, vol. 14:295-299.

Desmond et al., Improved Stress Tolerance of GroESL-Overproducing *Lactococcus Lactis* and Probiotic *Lactobacillus Paracasei* NFBC 338, Appl. Environ. Microbiol., 2004, vol. 70:5929-5936.

Sardessai et al., Organic Solvent-Tolerant Bacteria in Mangrove Ecosystem, Current Science, 2002, vol. 82:622-623.

Bieszkiewicz et al., Studies of The Resistance of Activated Sludge Bacteria to High Concentrationss of Methanol. Butanol. Glycol. Cyclohexanone and Cyclohexylamine, Acta Microbiologica Polonica, 1987, vol. 36:259-265.

Couto et al., Enhancement of Apparent Resistance to Ethanol in *Lactobacillus Hilgardii*, Biotechnology Letters, 1997, vol. 19:487-490.

Ingram, Effects of Alcohols on Micro-Organisms, Adv. Microbial. Physiol., 1984, vol. 25:253-300.

U.S. Appl. No. 11/527,995, filed Sep. 27, 2006, Gail K. Donaldson et al.

U.S. Appl. No. 60/796,816, filed May 2, 2006, Gail K. Donaldson et al.

U.S. Appl. No. 11/586,315, filed Oct. 25, 2006, Gail K. Donaldson et al.

U.S. Appl. No. 11/527,995, filed Sep. 27, 2006, Gail K. Donaldson et al.

U.S. Appl. No. 60/796,816, filed May 2, 2006, Gail K. Donaldon et al.

U.S. Appl. No. 11/586,315, filed Oct. 25, 2006, Gail K. Donaldson et al.

* cited by examiner

SOLVENT TOLERANT MICROORGANISMS AND METHODS OF ISOLATION

This application claims the benefit of U.S. Provisional Application No. 60/813,779, filed Jun. 15, 2006.

FIELD OF THE INVENTION

The invention relates to the field of industrial microbiology. Specifically, microorganisms have been isolated that demonstrate high tolerance to alcohols, particularly butanols.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known. For example, 1-butanol may be produced using the Oxo process, the Reppe process, or the hydrogenation of crotonaldehyde (*Ullmann's Encyclopedia of Industrial Chemistry, 6th* edition, 2003, Wiley-VCHVerlag GmbH and Co., Weinheim, Germany, Vol. 5, pp. 716-719). 2-Butanol may be produced using n-butene hydration (*Ullmann's Encyclopedia of Industrial Chemistry, 6th* edition, 2003, Wiley-VCHVerlag GmbH and Co., Weinheim, Germany, Vol. 5, pp. 716-719). Additionally, isobutanol may be produced using Oxo synthesis, catalytic hydrogenation of carbon monoxide (*Ullmann's Encyclopedia of Industrial Chemistry, 6th* edition, 2003, Wiley-VCHVerlag GmbH and Co., Weinheim, Germany, Vol. 5, pp. 716-719) or Guerbet condensation of methanol with n-propanol (Carlini et al., *J. Molec. Catal. A:Chem.* 220:215-220 (2004)). These processes use starting materials derived from petrochemicals, are generally expensive, and are not environmentally friendly.

Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (Donaldson et al., copending and commonly owned U.S. patent application Ser. No. 11/527,995), a 2-butanol biosynthetic pathway (Donaldson et al., copending and commonly owned U.S. Patent Application No. 60/796,816, and an isobutanol biosynthetic pathway (Maggio-Hall et al., copending and commonly owned U.S. patent application Ser. No. 11/586,315) have been described. However, biological production of butanols is believed to be limited by butanol toxicity to the host microorganism used in the fermentation.

Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., Current Microbiology 14(5):295-299 (1987)). Desmond et al. (*Appl. Environ. Microbiol.* 70(10):5929-5936 (2004)) report that overexpression of GroESL, a stress response protein, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) have been described. Additionally some *Lactobacillus* sp are known to be tolerant to ethanol (see for example, Couto, Pina and Hogg Biotechnology. Letter 19: 487-490). Ingram and Burke (1984) Adv. Micribial. Physiol 25: 253-300. However, for most microorganisms described in the art, growth is totally inhibited at a concentration of less than 2.0% w/v 1-butanol when grown in a liquid medium at 37° C. Moreover, microbial strains that have a tolerance to 2-butanol and isobutanol are not known in the art. Therefore, identification of microorganisms that have a high tolerance to 1-butanol, 2-butanol, and isobutanol would represent an advance in the art.

In addition, 2-butanone and ethanol are valuable compounds that can be produced by fermentation using microorganisms. 2-Butanone, also referred to as methyl ethyl ketone (MEK), is a widely used solvent and is the most important commercially produced ketone, after acetone. It is used as a solvent for paints, resins, and adhesives, as well as a selective extractant and activator of oxidative reactions. 2-butanone can be made by omitting the last step of the 2-butanol biosynthetic pathway (Donaldson et al., copending and commonly owned U.S. Patent Application No. 60/796,816). Ethanol is in high demand as an alternative fuel. Genetically modified strains of *E. coli* have been used as biocatalysts for ethanol production (Underwood et al., (2002) Appl. Environ. Microbiol. 68:6263-6272). A genetically modified strain of *Zymomonas mobilis* that has improved production of ethanol is described in US 2003/0162271 A1. Identification of microorganisms with improved tolerance to 2-butanone and ethanol would enhance the production of these compounds.

There is a need, therefore, for microbial host strains that are more tolerant to butanols and may be used for the bioproduction of butanols to high titer. The present invention addresses this need through the discovery of butanol tolerant microorganisms and development of methods for their isolation. In addition, the discovered microorganisms have increased tolerance to 2-butanone and ethanol.

SUMMARY OF THE INVENTION

The invention relates to butanol tolerant microorganisms, particularly members of the genus *Lactobacillus*, and methods for the isolation of the same. Microbial consortia were enriched and selected for tolerance to butanol. Several species of *Lactobacillus* were isolated that demonstrated tolerance to concentrations of butanol of at least 2.5% w/v 1-butanol when grown on a solid medium at 37° C.

Accordingly, the invention provides a method for the isolation of a butanol tolerant microorganism comprising:

a) providing a microbial sample comprising a microbial consortium;

b) contacting the microbial consortium with a growth medium comprising a fermentable carbon source until the members of the microbial consortium are growing;

c) contacting the growing microbial consortium of step (b) with butanol; and d) isolating the viable members of step (c) wherein a butanol tolerant microorganism is isolated.

In another embodiment the invention provides butanol tolerant microorganisms isolated by the methods of the invention, where preferred microorganisms are of the genus *Lactobacillus*.

In an alternate embodiment the invention provides a method for the isolation of a butanol tolerant *Lactobacillus* comprising:

a) providing a microbial sample comprising a microbial consortium;
b) enriching the microbial consortium for the presence of *Lactobacillus* in a medium containing a fermentable carbon source to generate a *Lactobacillus* enriched culture in which members of the *Lactobacillus* enriched culture are growing;
c) contacting the growing *Lactobacillus* enriched culture of step (b) with butanol; and
d) isolating the viable members of step (c) wherein a butanol tolerant *Lactobacillus* is isolated.

In a preferred embodiment the invention provides a butanol tolerant *Lactobacillus* isolated by the process of the invention, where the specific butanol tolerant *Lactobacillus* sp identified as ATCC PTA-8318 (*Lactobacillus plantarum* PN0510), ATCC PTA-8320 (*Lactobacillus plantarum* PN0511), ATCC PTA-7727 (*Lactobacillus plantarum* PN0512) and ATCC PTA-8319 (*Lactobacillus arizonensis* PN0514) are preferred.

In another embodiment the invention provides a method for the production of butanol comprising:

a) providing a *Lactobacillus* isolated by the process of the invention comprising genetic constructs encoding a butanol biosynthetic pathway; and
b) growing the *Lactobacillus* of step (a) under conditions whereby butanol is produced.

In yet another embodiment the invention provides a method for the production of 2-butanone comprising:

c) providing a *Lactobacillus* isolated by the process of the invention comprising genetic constructs encoding a 2-butanone biosynthetic pathway; and
d) growing the *Lactobacillus* of step (a) under conditions whereby 2-butanone is produced.

BRIEF DESCRIPTION BIOLOGICAL DEPOSITS AND SEQUENCE DESCRIPTIONS

The various embodiments of the invention can be more fully understood from the following detailed description, biological deposits, and the accompanying sequence descriptions, which form a part of this application.

Applicants made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Lactobacillus plantarum* PN0510 | ATCC: PTA-8318 | Apr. 3, 2007 |
| *Lactobacillus plantarum* PN0511 | ATCC: PTA-8320 | Apr. 3, 2007 |
| *Lactobacillus plantarum* PN0512 | ATCC: PTA-7727 | Jul. 12, 2006 |
| *Lactobacillus arizonensis* PN0514 | ATCC: PTA-8319 | Apr. 3, 2007 |

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Gene and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Gene and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *E. coli* ilvC (acetohydroxy acid reductoisomerase) | 31 | 32 |
| *E. coli* ilvD (acetohydroxy acid dehydratase) | 33 | 34 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

SEQ ID NOs:39 and 40 are the nucleotide sequences of primers used to amplify the 16S rRNA genes of butanol tolerant strains, as described in Example 1.

SEQ ID NOs: 41-44 are the nucleotide sequences of the 16S rRNA genes of butanol tolerant *Lactobacillus* strains, isolated as described in Example 1.

DETAILED DESCRIPTION OF THE INVENTION

The present invention provides microorganisms that demonstrate high tolerance to alcohols, particularly butanols, as well as to 2-butanone and ethanol. The microorganisms of the invention are able to grow in the presence of 2.5% w/v or greater 1-butanol on a solid medium. Additionally, the invention provides a method for the isolation of butanol tolerant microorganisms. These butanol tolerant microorganisms may be genetically engineered to comprise a butanol biosynthetic pathway or a 2-butanone iosynthetic pathway, and used for the bioproduction of 1-butanol, 2-butanol, isobutanol or 2-butanone to high titer.

The following definitions and abbreviations are to be used for the interpretation of the claims and the specification.

The term "butanol" as used herein, refers to 1-butanol, 2-butanol, isobutanol, or mixtures thereof.

The terms "butanol tolerant microorganism" and "tolerant" when used to describe a microorganism of the invention, refers to a bacterium or yeast that exhibits growth in the presence of 2.5% w/v or greater 1-butanol, 2-butanol, or isobutanol when grown on a solid medium at 37° C., or in the presence 2.0% w/v or greater 1-butanol, 2-butanol, or isobutanol when grown in a liquid medium at 37° C.

The term "microbial consortium" refers to a heterogenous group of microbes with different genotypes. By way of example, a microbial consortium may be an environmental sample such as a wastewater sludge or soil or compost or contaminated water sample; a chemically mutagenized microbial population of a pure bacterial strain; a microbial strain containing a multicopy plasmid library; or a population of transposon tagged mutants of a particular strain.

The term "environmental sample" refers to a sample obtained from the environment. In particular, the environmental sample may be wastewater sludge or other sample obtained from an environment where there has been exposure to butanol and/or other solvents. The environmental sample comprises a microbial consortium.

The term "enriching" as applied to a microbial culture and particularly the culturing of a microbial consortium refers to the practice of supplying the cells of the consortium or microbial culture with an excess of growth nutrients to enhance or encourage the growth of the cells.

The terms "fermentable carbon source", "carbon substrate" or "fermentable carbon substrate" are used interchangeably and refer to a source of carbon that is readily utilized by a microbial consortium. Fermentable carbon sources include, but are not limited to, monosaccharides, oligosaccharides, polysaccharides, and one-carbon substrates or mixtures thereof. A non-limiting list of preferred fermentable carbon sources includes simple sugars, such as glucose, fructose, and sucrose; and carboxylic acids such as fatty acids, butyric acid, and valeric acid.

The term "aerobic conditions" means growth conditions in the presence of oxygen.

The term "anaerobic conditions" means growth conditions in the absence of oxygen.

The term "microaerophilic conditions" means growth conditions with low levels of oxygen (i.e., below normal atmospheric oxygen levels).

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "2-butanone biosynthetic pathway" refers to an enzyme pathway to produce 2-butanone from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The term "invention" or "present invention" as used herein is meant to apply generally to all embodiments of the invention as described in the claims as presented or as later amended and supplemented, or in the specification.

In one embodiment the present invention provides a method for the isolation of butanol tolerant microorganisms. The method comprises enriching a microbial consortium under growth conditions and contacting the enriched consortium with butanol, as described in detail below. Microorganisms identified by the methods of the invention that demonstrate high tolerance to alcohols, particularly butanols, are also provided. These identified microorganisms also have high tolerance to 2-butanone and ethanol. These butanol tolerant microorganisms may be genetically engineered to comprise a butanol biosynthetic pathway or a 2-butanone biosynthetic pathway, and may be used for the bioproduction of 1-butanol, 2-butanol, isobutanol, or 2-butanone to high titer.

Isolation of Butanol Tolerant Microorganisms

Butanol tolerant microorganisms may be isolated from environmental samples such as wastewater sludge and samples from other environments where there is exposure to butanol and/or other solvents. For example, environmental samples may be obtained from wastewater treatment facilities at chemical plants. Industrial wastewater bioreactors are particularly good sources of environmental samples of microorganisms with desirable resistance phenotypes because of the long-term growth in the presence of various organic solvents (Bramucci et al., *Trends Biotechnol.* 18:501-505 (2000)). Butanol tolerant microorganisms may be isolated from other microbial samples as well. For example, the microbial sample may be a chemically mutagenized microbial population of a pure bacterial strain, a microbial strain containing a multicopy plasmid library, or a population of transposon tagged mutants of a particular strain. Any of these microbial samples including a mixed population is said to include a microbial consortium.

In one embodiment of the present invention, the microbial sample is cultured in a growth medium with an excess of growth nutrients thereby enriching the microbial consortium contained therein until the members of the consortium are growing. In one embodiment the cultures are growing in log phase. The growth medium comprises a fermentable carbon source and may include suitable levels of nitrogen, phosphorus, sulfur, and salts. Suitable levels of these nutrients necessary for growth of the microbial consortium are well known to those skilled in the art, and non-limiting examples are provided below. The fermentable carbon source may be any carbon source that is readily metabolized by the members of the microbial consortium, including but not limited to, sucrose, fructose, glucose, and mixtures thereof. The fermentable carbon source may also be a carboxylic acid such as a fatty acid, butyric acid or valeric acid. Typically, the carbon source is present at a concentration from about 0.1% weight/volume w/v to about 1.5% w/v. The nitrogen source may be any suitable nitrogen source, including but not limited to, ammonium salts or yeast extract. The nitrogen source is typically present in the growth medium at a concentration of about 10 mM. Phosphorus may be present in the medium in the form of phosphate salts, such as sodium and potassium phosphates, which are typically present in the growth medium at a concentration of about 50 mM. Sulfur may be present in the medium in the form of sulfate salts, such as sodium or ammonium sulfates, which are typically present in the growth medium at a concentration of about 10 mM. Additional salts include, but are not limited to, magnesium chloride, calcium chloride, manganese chloride, ferric chloride, ferrous chloride, zinc chloride, cupric chloride, cobalt chloride, and sodium molybdate. These salts are typically present in the growth medium at a concentration of about 1 μM to about 2 mM. The growth medium may also contain vitamins such as thiamine hydrochloride.

The enrichment culture is grown at a temperature of about 25° C. to about 60° C. for a time sufficient for the members of the microbial consortium in the sample to exhibit growth, typically about 12 hours to about 24 hours. The culture may be grown under anaerobic, microaerophilic, or aerobic conditions, with or without agitation. As is readily understood by the skilled person, anaerobic conditions are those that are devoid of oxygen, aerobic conditions are those that contain oxygen and microaerophilic conditions are those where oxygen is present at a level below that found in air, ie. less than 21%. Growth of the culture may be monitored by measuring the optical density, typically at a wavelength of 600 nm.

The growing enrichment culture is then contacted with butanol. This contacting may be done by diluting the enrichment culture with a fresh growth medium that contains butanol. It is particularly suitable if the enrichment culture is growing in log phase at this point. The butanol concentration used is about 0.8% w/v to about 3.0% w/v, preferably about 0.8% w/v to about 2.0% w/v. In one embodiment, the butanol is predominantly 1-butanol. In another embodiment, the butanol is predominantly 2-butanol. In another embodiment, the butanol is predominantly isobutanol. As used herein, predominantly means at least about 90% by weight of the total butanol. Additionally, mixtures comprising various combinations of two or more of 1-butanol, 2-butanol, and isobutanol may be used. The culture is grown for a period of time until significant growth is observed. Optionally, the cultures that demonstrate significant growth may be contacted with butanol again one or more times to select for increased tolerance to butanol. Each contacting may be made with progressively higher butanol concentrations.

The microbial consortium that was contacted with butanol is then separated to isolate individual strains. Multiple means of cell isolation are know to those skilled in the art involving either liquid or solid media. For example, the microbial consortium that was contacted with butanol may be plated onto a solid medium, for example nutrient agar, Luria Bertani (LB) agar, modified LB agar (i.e., LB agar supplemented with an fermentable carbon source and salts), or minimal enrichment medium with agar, which may or may not contain butanol. If butanol is present in the solid medium, its concentration is typically about 1.2% w/v to about 3% w/v. The culture is grown until colonies are formed. The colonies are then isolated using methods known in the art to provide a butanol tolerant microorganism. For example, the colonies from the solid medium may be collected and identified using methods known in the art, as described below. Alternatively, the colonies from the solid medium may be inoculated into a growth medium (e.g., minimal enrichment medium), either liquid or solid, that does not contain butanol. After growth, the cells may be collected and identified. Optionally, the cells from the colonies may be grown in the presence of butanol, either in liquid or solid growth medium (e.g., minimal enrichment medium). Typically, the butanol concentration in the medium is about 1.2% w/v to about 3% w/v. The cells that grow in the presence of butanol are collected. The isolated microorganisms may be identified using methods known in the art, such as 16S ribosomal RNA (rRNA) gene sequencing, fatty acid profile analysis, or ribotyping.

The butanol tolerant microorganisms isolated by the method of the present invention are tolerant to at least 2.5% butanol (i.e., 1-butanol, 2-butanol, or isobutanol) when grown on a solid medium at 37° C., or to at least 2.0% w/v butanol when grown in a liquid medium at 37° C. It should be noted that the butanol tolerance of microorganisms is typically higher when grown on a solid medium than when grown on a liquid medium. Additionally, the butanol tolerance of microorganisms is dependent on the growth temperature, typically being higher at lower growth temperatures. Microorganisms isolated by contacting the enriched microbial consortium with one butanol are generally also tolerant to other butanols as well as to 2-butanone and ethanol. For example, microorganisms isolated using 1-butanol are also tolerant to 2-butanol and isobutanol.

The tolerance of strains isolated using the present method may be assessed by determining the $IC_{50}$ values for growth in liquid medium containing added test chemical. The $IC_{50}$ value is the concentration of chemical that causes 50% growth inhibition. As shown in Examples 1 and 2 herein, $IC_{50}$ values of 1.8% w/v for 1-butanol, 2.4% w/v for isobutanol, 3.1% w/v for 2-butanol. 4.5% w/v for 2-butanone and 5.9% w/v for ethanol were determined in a selected strain. Based on the strain's growth on solid medium containing 1-butanol, these $IC_{50}$ values and a correlation seen between tolerance to 1-butanol and to each of the other tested compounds, the identified tolerant strains are expected to grow on solid medium containing 2.7% w/v isobutanol, 3.9% w/v 2-butanol, 5.0% w/v 2-butanone, or 9.0% w/v ethanol.

The enrichment culture may also be grown and contacted with butanol in a continuous culture in a chemostat bioreactor. The cells in a chemostat bioreactor can be grown at various growth rates by appropriate adjustment of the dilution rate. Chemostat cultures can be precisely controlled for aeration and pH, leading to higher cell densities. Additionally, butanol can be gradually added in increasing concentration by adjusting feed composition. After contacting the enrichment culture with butanol in the bioreactor, the butanol tolerant microorganisms are isolated and identified as described above.

Unexpectedly, many of the butanol tolerant microorganisms identified using the method of the present invention in the examples herein were bacteria belonging to the genus *Lactobacillus*. *Lactobacillus* bacteria are facultatively anaerobic, Gram-positive, non-motile, rod-shaped cells (*Bergey's Manual of Systematic Bacteriology*, Vol 2, Sneath et al., Eds.; Williams & Wilkins, Baltimore, Md., 1986, pp. 1063-1065). The butanol tolerant *Lactobacillus* strains were further characterized herein by determining the 16S rRNA gene sequences (SEQ ID NOs:41, 42, 43, and 44), which identified them as *Lactobacillus plantarum* and *Lactobacillus arizonensis* strains.

The present method for isolation of butanol tolerant microorganisms may be modified to selectively isolate butanol tolerant *Lactobacillus*. For example *Lactobacillus* may be enriched from a variety of environments using standard methods for culturing Lactobacilli using a lactic acid bacteria medium such as Bacto Lactobacilli MRS agar and then screened for tolerance to 1-butanol.

The isolated butanol tolerant *Lactobacillus* strains may be genetically engineered to comprise genetic constructs encoding a butanol biosynthetic pathway or a butanone biosynthetic pathway and grown under suitable conditions to produce butanol or butanone. The butanol biosynthetic pathway may be a 1-butanol, 2-butanol, or isobutanol biosynthetic pathway.

1-Butanol Biosynthetic Pathway

A biosynthetic pathway for the production of 1-butanol is described by Donaldson et al. in co-pending and commonly owned U.S. patent application Ser. No. 11/527,995, which is incorporated herein by reference. This biosynthetic pathway comprises the following substrate to product conversions:

a) acetyl-CoA to acetoacetyl-CoA, as catalyzed for example by acetyl-CoA acetyltransferase encoded by the genes given as SEQ ID NO:1 or 3;
b) acetoacetyl-CoA to 3-hydroxybutyryl-CoA, as catalyzed for example by 3-hydroxybutyryl-CoA dehydrogenase encoded by the gene given as SEQ ID NO:5;
c) 3-hydroxybutyryl-CoA to crotonyl-CoA, as catalyzed for example by crotonase encoded by the gene given as SEQ ID NO:7;
d) crotonyl-CoA to butyryl-CoA, as catalyzed for example by butyryl-CoA dehydrogenase encoded by the gene given as SEQ ID NO:9;
e) butyryl-CoA to butyraldehyde, as catalyzed for example by butyraldehyde dehydrogenase encoded by the gene given as SEQ ID NO:11; and
f) butyraldehyde to 1-butanol, as catalyzed for example by 1-butanol dehydrogenase encoded by the genes given as SEQ ID NO:13 or 15.

The pathway requires no ATP and generates $NAD^+$ and/or $NADP^+$, thus, it balances with the central, metabolic routes that generate acetyl-CoA.

2-Butanol and 2-Butanone Biosynthetic Pathway

Biosynthetic pathways for the production of 2-butanol and 2-butanone are described by Donaldson et al. in co-pending and commonly owned U.S. patent application Ser. Nos. 11/741,892 and 11/741,916, which are incorporated herein by reference. One 2-butanol biosynthetic pathway comprises the following substrate to product conversions:

a) pyruvate to alpha-acetolactate, as catalyzed for example by acetolactate synthase encoded by the gene given as SEQ ID NO:19;
b) alpha-acetolactate to acetoin, as catalyzed for example by acetolactate decarboxylase encoded by the gene given as SEQ ID NO:17;
c) acetoin to 2,3-butanediol, as catalyzed for example by butanediol dehydrogenase encoded by the gene given as SEQ ID NO:21;
d) 2,3-butanediol to 2-butanone, catalyzed for example by butanediol dehydratase encoded by genes given as SEQ ID NOs:23, 25, and 27; and
e) 2-butanone to 2-butanol, as catalyzed for example by 2-butanol dehydrogenase encoded by the gene given as SEQ ID NO:29.

Omitting the last step (e) of the above pathway provides a biosynthetic pathway for production of 2-butanone, also known as methyl ethyl ketone (MEK), Isobutanol Biosynthetic Pathway Biosynthetic pathways for the production of isobutanol are described by Maggio-Hall et al. in copending and commonly owned U.S. patent application Ser. No. 11/586,315, which is incorporated herein by reference. One isobutanol biosynthetic pathway comprises the following substrate to product conversions:

a) pyruvate to acetolactate, as catalyzed for example by acetolactate synthase encoded by the gene given as SEQ ID NO:19;
b) acetolactate to 2,3-dihydroxyisovalerate, as catalyzed for example by acetohydroxy acid isomeroreductase encoded by the gene given as SEQ ID NO:31;
c) 2,3-dihydroxyisovalerate to α-ketoisovalerate, as catalyzed for example by acetohydroxy acid dehydratase encoded by the gene given as SEQ ID NO:33;
d) α-ketoisovalerate to isobutyraldehyde, as catalyzed for example by a branched-chain keto acid decarboxylase encoded by the gene given as SEQ ID NO:35; and e) isobutyraldehyde to isobutanol, as catalyzed for example by a branched-chain alcohol dehydrogenase encoded by the gene given as SEQ ID NO:37.

Construction of *Lactobacillus* Hosts for Butanol or Butanone Production

Recombinant, butanol tolerant *Lactobacillus* strains containing the necessary genes that encode enzymes for one of the enzymatic pathways for the conversion of a fermentable carbon substrate to butanol or butanone may be constructed using techniques well known in the art. The genome sequences of *L. plantarum, L. salivarius, L sakei, L johnsonii, L. acidophilus* and *L. delbrueckii* are known (National Center for Biotechnology Information (NCBI) database), genbank™ identification as follows:

*Lactobacillus plantarum* WCFS1, complete genome gi|28376974|ref|NC_004567.1|[28376974]

*Lactobacillus salivarius* subsp. *salivarius* UCC118, complete genome gi|90960990|ref|NC_007929.1|[90960990]

*Lactobacillus sakei* strain 23K complete genome gi|78609255|emb|CR936503.1|[78609255]

*Lactobacillus johnsonii* NCC 533, complete genome gi|42518084|ref|NC_005362.1|[42518084]

*Lactobacillus acidophilus* NCFM, complete genome gi|58336354|ref|NC_006814.1|[58336354]

*Lactobacillus delbrueckii* subsp. *bulgaricus* ATCC 11842, complete genomegi|104773257|ref|NC_008054.1|[104773257]

These bacteria have a G+C content ranging from 32% to 49%.

In the present invention, genes encoding the enzymes of one of the butanol or butanone biosynthetic pathways described above may be isolated from various sources (see above). Methods of obtaining desired genes from a bacterial genome are common and well known in the art of molecular biology. For example, if the sequence of the gene is known, primers may be designed and the desired sequence amplified using standard primer-directed amplification methods such as polymerase chain reaction (U.S. Pat. No. 4,683,202) to obtain amounts of DNA suitable for cloning into transformation vectors. If a gene that is heterologous to a known sequence is to be isolated, suitable genomic libraries may be created by restriction endonuclease digestion and may be screened with probes having complementary sequence to the desired gene sequence. Once the sequence is isolated, the DNA may be amplified using standard primer-directed amplification methods such as polymerase chain reaction (U.S. Pat. No. 4,683,202) to obtain amounts of DNA suitable for cloning into expression vectors, which are then transformed into appropriate host cells.

In addition, given the amino acid sequence of a protein with desired enzymatic activity, the coding sequence may be ascertained by reverse translating the protein sequence. A DNA fragment containing the coding sequence may be prepared synthetically and cloned into an expression vector, then transformed into the desired host cell.

In preparing a synthetic DNA fragment containing a coding sequence, this sequence may be optimized for expression in the target host cell. Tools for codon optimization for expression in a heterologous host are readily available.

Once the relevant pathway genes are identified and isolated they may be inserted in a vector and transformed into a butanol tolerant *Lactobacillus* host by means well known in the art. Vectors useful for the transformation of *Lactobacillus* are known (see below). Typically the vector or cassette contains sequences directing transcription and translation of the inserted DNA fragment, a selectable marker, and sequences allowing autonomous replication or chromosomal integration. Suitable vectors comprise a region 5' of the inserted DNA fragment which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific production host.

Initiation control regions or promoters, which are useful to drive expression of the relevant pathway coding regions in the desired *Lactobacillus* host cell, may be obtained from other lactic acid bacteria or other Gram-positive organisms. A non-limiting example is the nisA promoter from *Lactococcus*. Termination control regions may also be derived from various genes native to the preferred hosts or related bacteria. Optionally, a termination site may be unnecessary, however, it is most preferred if included.

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. *Appl. Environ. Microbiol.* 2005 March; 71(3): 1223-1230), which may be used for transformation.

The various genes for a butanol or butanone biosynthetic pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224:1252-154 (1990)), Bringel and Hubert (*Appl. Microbiol. Biotechnol.* 33: 664-670 (1990)), and Teresa Alegre, Rodriguez and Mesas (*FEMS Microbiology letters* 241:73-77 (2004)). Plasmids can also be introduced to *Lactobacillus plantatrum* by conjugation (Shrago, Chassy and Dobrogosz *Appl. Environ. Micro.* 52: 574-576 (1986)). The butanol or butanone biosynthetic pathway genes can also be integrated into the chromosome of *Lactobacillus* using integration vectors (Hols et al. *Appl. Environ. Micro.* 60:1401-1403 (1990); Jang et al. *Micro. Lett.* 24:191-195 (2003)).

Fermentation Media

Fermentation media for the production of butanol or butanone must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Sucrose may be obtained from feedstocks such as sugar cane, sugar beets, cassava, and sweet sorghum. Glucose and dextrose may be obtained through saccharification of starch based feedstocks including grains such as corn, wheat, rye, barley, and oats.

In addition, fermentable sugars may be obtained from cellulosic and lignocellulosic biomass through processes of pretreatment and saccharification, as described, for example, in co-owned and co-pending US patent application US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol or butanone production.

Culture Conditions

Typically cells are grown at a temperature in the range of about 25° C. to about 40° C. in an appropriate medium. Suitable growth media in the present invention are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Industrial Batch and Continuous Fermentations

Butanol or butanone may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Butanol or butanone may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol or butanone may be practiced using either batch, fed-batch or continuous processes and that any known mode of fermentation would be suitable. Additionally, it is contemplated that cells may be immobilized on a substrate as whole cell catalysts and subjected to fermentation conditions for butanol or butanone production.

Methods for Butanol and 2-Butanone Isolation from the Fermentation Medium

Bioproduced butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation. These same methods may be adapted to isolate bioproduced 2-butanone from the fermentation medium.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec' means second(s), "µL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "rpm" means revolutions per minute, "w/v" means weight/volume, "OD" means optical density, "$OD_{600}$" means optical density measured at a wavelength of 600 nm, "$OD_{595}$" means optical density measured at a wavelength of 595 nm, "$IC_{50}$" means the concentration of butanol that causes a 50% inhibition of growth, "GCMS" means gas chromatography-mass spectrometry, and "HPLC" means high performance liquid chromatography.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Isolation of Butanol Tolerant Bacterial Strains Using Continuous Culture

The purpose of these Examples was to isolate butanol tolerant bacterial strains. Environmental samples were obtained from several wastewater treatment sites and were grown in the presence of 1-butanol in continuous culture in a chemostat bioreactor. Several 1-butanol tolerant bacterial strains were isolated and identified as *Lactobacillus plantarum* or *Lactobacillus arizonensis*.

An Appilikon Fermentor (Appilikon Inc., Clinton, N.J.) was operated as an anaerobic chemostat. The bioreactor system was composed of a 1-L dished bottom reactor, Controller ADI 1032 P100, and stirrer unit with marine and turbine impellers. Bio Controller ADI 1030 Z510300020 with appropriate sensors monitored pH, dissolved oxygen, and temperature. A Cole Parmer pump and pump head (Cole Parmer Instrument Co., Vernon Hills, Ill.) were used for addition of acid and base to maintain pH 7.0. The temperature was maintained at 37° C. using a circulating water bath. The culture medium (S20 medium) consisted of 5 mM potassium phosphate buffer, pH 7.0, 10 mM ammonium sulfate, 0.1% yeast extract, 0.1% caseamino acids, 100 mM MOPS, 2 mM $MgCl_2$, 0.7 mM $CaCl_2$, 0.05 mM $MnCl_2$, 0.001 mM $ZnCl_2$, 0.002 mM thiamine hydrochloride, 1.72 μM $CuCl_2$, 2.53 μM $COCl_2$, 2.42 μM $Na_2MoO_4$, 25 mM glucose, 12.5 mM sucrose, and 12.5 mM fructose. A volume of 500 mL of this medium was used in the bioreactor. The bioreactor was operated with a feed rate in the range of 0.1 to 1.0 mL/minute and a stirrer speed of 50 rpm.

The bioreactor was inoculated with a mixture of several wastewater sludge samples obtained from different wastewater treatment facilities at several E.I. du Pont de Nemours and Company sites. After a short period of batch mode operation, the bioreactor was operated in continuous feed mode with 1-butanol gradually added in increasing concentration to the culture medium. The flow rate of the medium was in the range of 0.1 to 1.0 mL/min.

Cell density in the bioreactor was monitored by measuring the optical density at 600 nm. The 1-butanol in the feed and effluent was determined by GCMS using an HP6890 Gas Chromatograph with 5973 Mass Detector (Agilent Technologies, Inc, Wilmington, Del.). The GC column was a DB-WAX, 30 m×0.32 mm ID×0.25 μm column (J&W Scientific, Inc., Folsom, Calif.). Alternatively, samples were filtered (Acrodisc CR PTFE 0.2 μm filters) and analyzed by HPLC using a Shodex® SH1011 column (8 mm ID×300 mm length; Shoko America Inc., Colorado Springs, Colo.) with a Shodex® SH-G guard column. The mobile phase was 0.01 N sulfuric acid. The column temperature was 50° C. and a flow rate of 0.5 mL/min was used. For detection, a photometric detector at 210 nm and a refractive index detector were used. The sample injection volume was 10 μL.

After an initial adjustment period, the amount of 1-butanol entering the bioreactor through the feed was gradually increased to 2.5% w/v. During this same period, the amount of glucose in the bioreactor effluent was monitored. Increasing the amount of 1-butanol in the feed resulted in a decrease in cell density and a concomitant decrease in glucose utilization. Continued incubation resulted in the cell density and glucose utilization again increasing after adaptation to the higher level of 1-butanol. For example, increasing 1-butanol to 1.6% resulted in the cell density decreasing to less than 1.5 $OD_{600}$ with a corresponding decrease in glucose utilization. However, continued incubation resulted in the cell density increasing to 2.3 $OD_{600}$ with a corresponding increase in glucose consumption.

Isolation of pure strains of 1-butanol resistant bacteria from this bioreactor were performed as follows. Samples of cells from the bioreactor waste jug were serially diluted, and the serial dilutions were plated on trypticase soy agar (Difco; Bekton Dickinson and Company; San Jose, Calif.) without 1-butanol. Colonies were then inoculated from the agar media into 1.2 mL of S20 medium without 1-butanol in the wells of a square-well microtiter plate (Beckman Coulter Inc, Fullerton, Calif.; Catalog No. 069681). The square-well microtiter plate was sealed with an adhesive cover (Beckman Coulter Inc.; Catalog No. 538619) and incubated at 37° C. with shaking for up to 72 h. The square-well microtiter plate was used to make a master plate by dispensing 200 μL of culture from each square well into a corresponding well in a "U-bottom" microtiter plate (VWR Scientific Products, West Chester, Pa.; Catalog No. 62409-052). Isolates from the master plate were replica-plated onto S20 agar or TSA agar plates containing between 1.2% and 3.4% 1-butanol using the Nunc-TSP transferable solid phase screening system (Nalgene Nunc International, Napersville, Ill.; Catalog No. 445-497). Tolerant isolates were identified by growth at 37° C. after 24 to 72 h. The several isolates that grew on agar medium with 3% 1-butanol were characterized further.

The $IC_{50}$ values of the isolated strains were determined at 37° C., as follows. The isolates were cultured in S30L medium (i.e., 10 mM ammonium sulfate, 5 mM potassium phosphate buffer, pH 7.0, 50 mM MOPS, pH 7.0, 2 mM $MgCl_2$, 0.7 mM $CaCl_2$, 50 μM $MnCl_2$, 1 μM $FeCl_3$, 1 μM $ZnCl_2$, 1.72 μM $CuCl_2$, 2.53 μM $COCl_2$, 2.42 μM $Na_2MoO_4$, 2 μM thiamine hydrochloride, 0.01 M glucose, and 0.2% yeast extract) at 37° C. in the absence (control) and in the presence of various amounts of 1-butanol, and the doubling time for each culture was calculated from the logarithmic part of the growth curve (doubling time=0.693/growth rate). The percent growth inhibition caused by 1-butanol in the sample flasks was determined by subtracting the percent growth ([doubling time of the control flask/doubling time of the sample flask]×100) from 100%. The $IC_{50}$ was the concentration of butanol that caused 50% growth inhibition and was determined by plotting the concentration of butanol versus percent inhibition. The results are summarized in Table 4.

TABLE 4

Butanol Tolerant Bacterial Strains Isolated from Environmental Samples

| Strain | Phylotype | ATCC No. | 16S rRNA Sequence | $IC_{50}$ (%) 1-butanol |
|---|---|---|---|---|
| PN0510 | *Lactobacillus plantarum* | PTA-8318 | SEQ ID NO: 41 | 1.4 |
| PN0511 | *Lactobacillus plantarum* | PTA-8320 | SEQ ID NO: 42 | 1.6 |
| PN0512 | *Lactobacillus plantarum* | PTA-7727 | SEQ ID NO: 43 | 1.8 |
| PN0514 | *Lactobacillus arizonensis* | PTA-8319 | SEQ ID NO: 44 | 1.7 |

The isolates were identified by sequencing the product that resulted from polymerase chain reaction (PCR) amplification of the 16S rRNA genes in DNA that was extracted from each isolate. DNA was extracted from each of the 1-butanol tolerant strains. Each isolate was processed using a commercial kit (Ultraclean Microbial Genomic DNA Isolation Kit obtained from Mo Bio Laboratories, Inc, Carlsbad, Calif., Part No. 12224-50). The 16S rRNA genes of the isolates were amplified by PCR using HotStar Taq (Qiagen, Valencia, Calif.; Catalog No. 203446) with primers JCR14 (ACGGGCGGTGTGTAC), given as SEQ ID NO:39 and JCR15 (GCCAGCAGCCGCGGTA), given as SEQ ID NO:40. The PCR conditions were 15 min at 95° C., followed by 30 cycles at 94° C. for 45 sec, 55° C. for 1 min, and 72° C. for 1 min, followed by 10 min at 72° C. The PCR products were purified and sequenced. Each sequence was used as the query sequence for a BLAST search of GenBank to determine the most similar previously identified 16S rRNA gene sequence. Three strains selected as being butanol tolerant were identified as *Lactobacillus plantarum* and one strain as *Lactobacillus arizonensis* (see Table 4).

Example 2

Tolerance of 1-Butanol Tolerant *Lactobacillus* to Other Compounds

The purpose of this Example was to test the tolerance of a *Lactobacillus* strain isolated based on tolerance to 1-butanol, to the additional compounds 2-butanol, isobutanol, 2-butanone and ethanol. The $IC_{50}$ values of these compounds were determined for the selected 1-butanol tolerant *Lactobacillus plantarum* PN0512 strain as described in Example 1 for 1-butanol. The results are summarized in Table 5.

Based on the $IC_{50}$ values determined for each compound and a correlation seen between tolerance to 1-butanol and to each of the other tested compounds, the identified tolerant strains are expected to grow on solid medium containing 3.9% w/v 2-butanol, 2.7% w/v isobutanol, 5.0% w/v 2-butanone, or 9.0% w/v ethanol.

TABLE 5

Tolerance of PN0512 to 2-butanol, isobutanol and 2-butanone.

| Compound | $IC_{50}$ (%) |
|---|---|
| Isobutanol | 2.4 |
| 2-Butanol | 3.1 |
| 2-butanone | 4.5 |
| Ethanol | 5.9 |

What is claimed is:

1. A method for the isolation of a butanol tolerant *Lactobacillus* microorganism comprising:

a) providing a microbial sample comprising a microbial consortium;

b) contacting the microbial consortium with a growth medium comprising a fermentable carbon source until the members of the microbial consortium are growing;

c) contacting the growing microbial consortium of step (b) with butanol; and d) isolating the viable members of step (c) wherein a butanol tolerant microorganism is isolated wherein the viable members of step (d) are tolerant to at least one of the following:

i) 2.5% w/v 1-butanol when grown on a solid medium at 37.degree. C.;

ii) 3.9% w/v 2-butanol when grown on a solid medium at 37.degree. C.;

iii) 2.7% w/v isobutanol when grown on a solid medium at 37.degree. C.;

iv) 5.0% w/v 2-butanone when grown on a solid medium at 37.degree. C.; or v) 9.0% w/v ethanol I when grown on a solid medium at 37.degree. C.

2. A method according to claim 1 wherein the growing consortium of step (b) are growing in log phase.

3. A method according to claim 1 wherein after step (c) the consortium is plated on solid medium.

4. A method according to claim 3 wherein the solid medium contains butanol.

5. A method according to claim 1 wherein the contacting of step (c) is repeated one or more times.

6. A method according to claim 1 wherein the butanol concentration of the contacting step (c) is from about 0.8% w/v to about 3.0% w/v.

7. A method according to claim 1 wherein the isolating of step (d) comprises the steps of:

i) growing the viable members of step (d) in a liquid medium in the absence of butanol; whereby the viable members multiply;

ii) growing the cells of step (i) in the presence of butanol; and iii) collecting the cells of step (ii) that grow in the presence of butanol wherein a butanol tolerant microorganism is isolated.

8. A method according to claim 1 wherein the fermentable carbon source is selected from the group consisting of sucrose, fructose, glucose, butyric acid, valeric acid and mixtures thereof.

9. A method according to claim 1 wherein the butanol is predominantly 1-butanol.

10. A method according to claim 1 wherein the butanol is predominantly 2-butanol.

11. A method according to claim 1 wherein the butanol is predominantly isobutanol.

12. A method according to claim 1 wherein the consortium is grown under anaerobic conditions.

13. A method according to claim 1 wherein the consortium is grown under microaerophilic conditions.

14. A method according to claim 1 wherein the consortium is grown under aerobic conditions.

15. A method according to claim 1 wherein the microbial sample is an environmental sample.

16. A method for the isolation of a butanol tolerant *Lactobacillus* comprising:

a) providing a microbial sample comprising a microbial consortium;

b) enriching the microbial consortium for the presence of *Lactobacillus* in a medium containing a fermentable carbon source to generate a *Lactobacillus* enriched culture in which members of the *Lactobacillus* enriched culture are growing;

c) contacting the growing *Lactobacillus* enriched culture of step (b) with butanol; and d) isolating the viable members of step (c) wherein a butanol tolerant *Lactobacillus* is isolated wherein the viable members of sten (d) are tolerant to at least one of the following:

i) 2.5% w/v 1-butanol when grown on a solid medium at 37.degree. C.;

ii) 3.9% w/v 2-butanol when grown on a solid medium at 37.degree. C.;

iii) 2.7% w/v isobutanol when grown on a solid medium at 37.degree. C.;

iv) 5.0% w/v 2-butanone when grown on a solid medium at 37.degree. C.; or v) 9.0% w/v ethanol I when grown on a solid medium at 37.degree. C.

17. A method according to claim 16 wherein the growing *Lactobacillus* of step (c) are growing in log phase.

18. A method according to claim 16 wherein the microbial sample is an environmental sample.

19. A method according to claim 16 wherein after step (c) the members of the consortium are plated on solid medium.

20. A method according to claim 19 wherein the solid medium contains butanol.

21. A method according to claim 20 wherein the solid medium is a lactic acid bacteria medium containing butanol.

22. A method according to claim 16 wherein the contacting of step (c) is repeated one or more times.

23. A method according to claim 16 wherein the contacting of step (c) is done with the butanol at a concentration between about 0.8% w/v to about 3.0% w/v.

24. A method according to claim 16 wherein the isolating of step (d) comprises the steps of:

i) growing the viable members of step (d) in a liquid medium in the absence of butanol whereby the viable members multiply;

ii) growing the cells of step (I) in the presence of butanol; and iii) collecting the cells of step (ii) that grow in the presence of butanol wherein a butanol tolerant microorganism is isolated.

25. A method according to claim 16 wherein the fermentable carbon source is selected from the group consisting of sucrose, fructose, glucose, butyric acid, valeric acid and mixtures thereof.

26. A method according to claim 16 wherein the butanol is predominantly 1-butanol.

27. A method according to claim 16 wherein the butanol is predominantly 2-butanol.

28. A method according to claim 16 wherein the butanol is predominantly isobutanol.

* * * * *

SEQUENCE LISTING

```
<160> NUMBER OF SEQ ID NOS: 44

<210> SEQ ID NO 1
<211> LENGTH: 1179
<212> TYPE: DNA
<213> ORGANISM: Clostridium acetobutylicum

<400> SEQUENCE: 1

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300
```

-continued

```
atttaaaag caggagatgc tgacgtaata atagcaggtg gtatggaaaa tatgtctaga    360

gctccttact tagcgaataa cgctagatgg ggatatagaa tgggaaacgc taaatttgtt    420

gatgaaatga tcactgacgg attgtgggat gcatttaatg attaccacat gggaataaca    480

gcagaaaaca tagctgagag atggaacatt tcaagagaag aacaagatga gtttgctctt    540

gcatcacaaa aaaaagctga agaagctata aaatcaggtc aatttaaaga tgaaatagtt    600

cctgtagtaa ttaaaggcag aaagggagaa actgtagttg atacagatga gcaccctaga    660

tttggatcaa ctatagaagg acttgcaaaa ttaaaacctg ccttcaaaaa agatggaaca    720

gttacagctg gtaatgcatc aggattaaat gactgtgcag cagtacttgt aatcatgagt    780

gcagaaaaag ctaaagagct tggagtaaaa ccacttgcta agatagtttc ttatggttca    840

gcaggagttg acccagcaat aatgggatat ggacctttct atgcaacaaa agcagctatt    900

gaaaaagcag gttggacagt tgatgaatta gatttaatag aatcaaatga agcttttgca    960

gctcaaagtt tagcagtagc aaaagattta aaatttgata tgaataaagt aaatgtaaat   1020

ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179
```

```
<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220
```

-continued

```
Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390
```

<210> SEQ ID NO 3
<211> LENGTH: 1179
<212> TYPE: DNA
<213> ORGANISM: Clostridium acetobutylicum

<400> SEQUENCE: 3

```
atgagagatg tagtaatagt aagtgctgta agaactgcaa taggagcata tggaaaaaca     60

ttaaaggatg tacctgcaac agagttagga gctatagtaa taaaggaagc tgtaagaaga    120

gctaatataa atccaaatga gattaatgaa gttatttttg gaaatgtact tcaagctgga    180

ttaggccaaa acccagcaag acaagcagca gtaaaagcag gattaccttt agaaacacct    240

gcgtttacaa tcaataaggt ttgtggttca ggtttaagat ctataagttt agcagctcaa    300

attataaaag ctggagatgc tgataccatt gtagtaggtg gtatggaaaa tatgtctaga    360

tcaccatatt tgattaacaa tcagagatgg ggtcaaagaa tgggagatag tgaattagtt    420

gatgaaatga taaaggatgg tttgtgggat gcatttaatg gatatcatat gggagtaact    480

gcagaaaata ttgcagaaca atggaatata acaagagaag agcaagatga attttcactt    540

atgtcacaac aaaaagctga aaaagccatt aaaaatggag aatttaagga tgaaatagtt    600

cctgtattaa taaagactaa aaaaggtgaa atagtctttg atcaagatga atttcctaga    660

ttcggaaaca ctattgaagc attaagaaaa cttaaaccta ttttcaagga aaatggtact    720

gttacagcag gtaatgcatc cggattaaat gatggagctg cagcactagt aataatgagc    780

gctgataaag ctaacgctct cggaataaaa ccacttgcta agattacttc ttacggatca    840

tatggggtag atccatcaat aatgggatat ggagcttttt atgcaactaa agctgcctta    900

gataaaatta atttaaaacc tgaagactta gatttaattg aagctaacga ggcatatgct    960

tctcaaagta tagcagtaac tagagattta aatttagata tgagtaaagt taatgttaat   1020

ggtggagcta tagcacttgg acatccaata ggtgcatctg gtgcacgtat tttagtaaca   1080

ttactatacg ctatgcaaaa aagagattca aaaaaaggtc ttgctactct atgtattggt   1140
```

ggaggtcagg gaacagctct cgtagttgaa agagactaa 1179

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365
```

-continued

```
Asp Ser Lys Lys Gly Leu Ala Thr Leu Cys Ile Gly Gly Gly Gln Gly
    370                 375                 380

Thr Ala Leu Val Val Glu Arg Asp
385                 390
```

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt     60

gcagctaaag gatttgaagt agtattaaga gatattaaag atgaatttgt tgatagagga    120

ttagatttta tcaataaaaa tctttctaaa ttagttaaaa aaggaaagat agaagaagct    180

actaaagttg aaatcttaac tagaatttcc ggaacagttg accttaatat ggcagctgat    240

tgcgatttag ttatagaagc agctgttgaa agaatggata ttaaaaagca gatttttgct    300

gacttagaca atatatgcaa gccagaaaca attcttgcat caaatacatc atcactttca    360

ataacagaag tggcatcagc aactaaaaga cctgataagg ttataggtat gcatttcttt    420

aatccagctc ctgttatgaa gcttgtagag gtaataagag gaatagctac atcacaagaa    480

acttttgatg cagttaaaga gacatctata gcaataggaa aagatcctgt agaagtagca    540

gaagcaccag gatttgttgt aaatagaata ttaataccaa tgattaatga agcagttggt    600

atattagcag aaggaatagc ttcagtagaa gacatagata aagctatgaa acttggagct    660

aatcacccaa tgggaccatt agaattaggt gattttatag gtcttgatat atgtcttgct    720

ataatggatg ttttatactc agaaactgga gattctaagt atagaccaca tacattactt    780

aagaagtatg taagagcagg atggcttgga agaaaatcag gaaaaggttt ctacgattat    840

tcaaaataa                                                             849
```

<210> SEQ ID NO 6
<211> LENGTH: 282
<212> TYPE: PRT
<213> ORGANISM: Clostridium acetobutylicum

<400> SEQUENCE: 6

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140
```

```
Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280


<210> SEQ ID NO 7
<211> LENGTH: 786
<212> TYPE: DNA
<213> ORGANISM: Clostridium acetobutylicum

<400> SEQUENCE: 7

atggaactaa acaatgtcat ccttgaaaag gaaggtaaag ttgctgtagt taccattaac      60

agacctaaag cattaaatgc gttaaatagt gatacactaa aagaaatgga ttatgttata     120

ggtgaaattg aaaatgatag cgaagtactt gcagtaattt taactggagc aggagaaaaa     180

tcatttgtag caggagcaga tatttctgag atgaaggaaa tgaataccat tgaaggtaga     240

aaattcggga tacttggaaa taaagtgttt agaagattag aacttcttga aaagcctgta     300

atagcagctg ttaatggttt tgctttagga ggcggatgcg aaatagctat gtcttgtgat     360

ataagaatag cttcaagcaa cgcaagattt ggtcaaccag aagtaggtct cggaataaca     420

cctggttttg gtggtacaca aagactttca agattagttg gaatgggcat ggcaaagcag     480

cttatattta ctgcacaaaa tataaaggca gatgaagcat taagaatcgg acttgtaaat     540

aaggtagtag aacctagtga attaatgaat acagcaaaag aaattgcaaa caaaattgtg     600

agcaatgctc cagtagctgt taagttaagc aaacaggcta ttaatagagg aatgcagtgt     660

gatattgata ctgctttagc atttgaatca gaagcatttg gagaatgctt ttcaacagag     720

gatcaaaagg atgcaatgac agctttcata gagaaaagaa aaattgaagg cttcaaaaat     780

agatag                                                                786


<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
```

```
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260


<210> SEQ ID NO 9
<211> LENGTH: 1197
<212> TYPE: DNA
<213> ORGANISM: Clostridium acetobutylicum

<400> SEQUENCE: 9

atgatagtaa aagcaaagtt tgtaaaagga tttatcagag atgtacatcc ttatggttgc      60

agaagggaag tactaaatca aatagattat tgtaagaagg ctattgggtt taggggacca     120

aagaaggttt taattgttgg agcctcatct gggtttggtc ttgctactag aatttcagtt     180

gcatttggag gtccagaagc tcacacaatt ggagtatcct atgaaacagg agctacagat     240

agaagaatag gaacagcggg atggtataat aacatatttt ttaaagaatt tgctaaaaaa     300

aaaggattag ttgcaaaaaa cttcattgag gatgcctttt ctaatgaaac caaagataaa     360

gttattaagt atataaagga tgaatttggt aaaatagatt tatttgttta tagtttagct     420

gcgcctagga gaaaggacta taaaactgga aatgtttata cttcaagaat aaaaacaatt     480

ttaggagatt ttgagggacc gactattgat gttgaaagag acgagattac tttaaaaaag     540

gttagtagtg ctagcattga agaaattgaa gaaactagaa aggtaatggg tggagaggat     600

tggcaagagt ggtgtgaaga gctgctttat gaagattgtt tttcggataa agcaactacc     660

atagcatact cgtatatagg atccccaaga acctacaaga tatatagaga aggtactata     720

ggaatagcta aaaaggatct tgaagataag gctaagctta taaatgaaaa acttaacaga     780

gttataggtg gtagagcctt tgtgtctgtg aataaagcat tagttacaaa agcaagtgca     840
```

```
tatattccaa cttttcctct ttatgcagct attttatata aggtcatgaa agaaaaaaat    900

attcatgaaa attgtattat gcaaattgag agaatgtttt ctgaaaaaat atattcaaat    960

gaaaaaatac aatttgatga caagggaaga ttaaggatgg acgatttaga gcttagaaaa   1020

gacgttcaag acgaagttga tagaatatgg agtaatatta ctcctgaaaa ttttaaggaa   1080

ttatctgatt ataagggata caaaaaagaa ttcatgaact taaacggttt tgatctagat   1140

ggggttgatt atagtaaaga cctggatata gaattattaa gaaaattaga accttaa      1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
```

-continued

```
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395


<210> SEQ ID NO 11
<211> LENGTH: 1407
<212> TYPE: DNA
<213> ORGANISM: Clostridium beijerinckii

<400> SEQUENCE: 11

atgaataaag acacactaat acctacaact aaagatttaa aagtaaaaac aaatggtgaa      60

aacattaatt taaagaacta caaggataat tcttcatgtt tcggagtatt cgaaaatgtt     120

gaaaatgcta taagcagcgc tgtacacgca caaaagatat tatcccttca ttatacaaaa     180

gagcaaagag aaaaaatcat aactgagata agaaaggccg cattacaaaa taaagaggtc     240

ttggctacaa tgattctaga agaaacacat atgggaagat atgaggataa aatattaaaa     300

catgaattgg tagctaaata tactcctggt acagaagatt taactactac tgcttggtca     360

ggtgataatg gtcttacagt tgtagaaatg tctccatatg gtgttatagg tgcaataact     420

ccttctacga atccaactga aactgtaata tgtaatagca taggcatgat agctgctgga     480

aatgctgtag tatttaacgg acacccatgc gctaaaaaat gtgttgcctt tgctgttgaa     540

atgataaata aggcaattat ttcatgtggc ggtcctgaaa atctagtaac aactataaaa     600

aatccaacta tggagtctct agatgcaatt attaagcatc cttcaataaa acttctttgc     660

ggaactgggg gtccaggaat ggtaaaaacc ctcttaaatt ctggtaagaa agctataggt     720

gctggtgctg gaaatccacc agttattgta gatgatactg ctgatataga aaaggctggt     780

aggagcatca ttgaaggctg ttcttttgat aataatttac cttgtattgc agaaaaagaa     840

gtatttgttt ttgagaatgt tgcagatgat ttaatatcta acatgctaaa aaataatgct     900

gtaattataa atgaagatca agtatcaaaa ttaatagatt tagtattaca aaaaaataat     960

gaaactcaag aatactttat aaacaaaaaa tgggtaggaa aagatgcaaa attattctta    1020

gatgaaatag atgttgagtc tccttcaaat gttaaatgca taatctgcga agtaaatgca    1080

aatcatccat ttgttatgac agaactcatg atgccaatat tgccaattgt aagagttaaa    1140

gatatagatg aagctattaa atatgcaaag atagcagaac aaaatagaaa acatagtgcc    1200

tatatttatt ctaaaaatat agacaaccta aatagatttg aaagagaaat agatactact    1260

atttttgtaa agaatgctaa atcttttgct ggtgttggtt atgaagcaga aggatttaca    1320

actttcacta ttgctggatc tactggtgag ggaataacct ctgcaaggaa ttttacaaga    1380

caaagaagat gtgtacttgc cggctaa                                        1407


<210> SEQ ID NO 12
<211> LENGTH: 468
<212> TYPE: PRT
<213> ORGANISM: Clostridium beijerinckii
```

-continued

<400> SEQUENCE: 12

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415
```

-continued

```
Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465
```

<210> SEQ ID NO 13
<211> LENGTH: 1215
<212> TYPE: DNA
<213> ORGANISM: Clostridium acetobutylicum

<400> SEQUENCE: 13

```
atggttgatt tcgaatattc aataccaact agaatttttt tcggtaaaga taagataaat      60

gtacttggaa gagagcttaa aaaatatggt tctaaagtgc ttatagttta tggtggagga     120

agtataaaga gaaatggaat atatgataaa gctgtaagta tacttgaaaa aaacagtatt     180

aaattttatg aacttgcagg agtagagcca aatccaagag taactacagt tgaaaaagga     240

gttaaaatat gtagagaaaa tggagttgaa gtagtactag ctataggtgg aggaagtgca     300

atagattgcg caaaggttat agcagcagca tgtgaatatg atggaaatcc atgggatatt     360

gtgttagatg gctcaaaaat aaaaagggtg cttcctatag ctagtatatt aaccattgct     420

gcaacaggat cagaaatgga tacgtgggca gtaataaata atatggatac aaacgaaaaa     480

ctaattgcgg cacatccaga tatggctcct aagttttcta tattagatcc aacgtatacg     540

tataccgtac ctaccaatca aacagcagca ggaacagctg atattatgag tcatatattt     600

gaggtgtatt ttagtaatac aaaaacagca tatttgcagg atagaatggc agaagcgtta     660

ttaagaactt gtattaaata tggaggaata gctcttgaga agccggatga ttatgaggca     720

agagccaatc taatgtgggc ttcaagtctt gcgataaatg gacttttaac atatggtaaa     780

gacactaatt ggagtgtaca cttaatggaa catgaattaa gtgcttatta cgacataaca     840

cacggcgtag ggcttgcaat tttaacacct aattggatgg agtatatttt aaataatgat     900

acagtgtaca agtttgttga atatggtgta aatgtttggg gaatagacaa agaaaaaaat     960

cactatgaca tagcacatca agcaatacaa aaaacaagag attactttgt aaatgtacta    1020

ggtttaccat ctagactgag agatgttgga attgaagaag aaaaattgga cataatggca    1080

aaggaatcag taaagcttac aggaggaacc ataggaaacc taagaccagt aaacgcctcc    1140

gaagtcctac aaatattcaa aaaatctgtg taaaacgcct ccgaagtcct acaaatattc    1200

aaaaaatctg tgtaa                                                    1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45
```

-continued

```
Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390
```

<210> SEQ ID NO 15
<211> LENGTH: 1170
<212> TYPE: DNA
<213> ORGANISM: Clostridium acetobutylicum

<400> SEQUENCE: 15

```
atgctaagtt ttgattattc aataccaact aaagtttttt ttggaaaagg aaaaatagac      60

gtaattggag aagaaattaa gaaatatggc tcaagagtgc ttatagttta tggcggagga     120
```

-continued

```
agtataaaaa ggaacggtat atatgataga gcaacagcta tattaaaaga aaacaatata    180

gctttctatg aactttcagg agtagagcca aatcctagga taacaacagt aaaaaaaggc    240

atagaaatat gtagagaaaa taatgtggat ttagtattag caataggggg aggaagtgca    300

atagactgtt ctaaggtaat tgcagctgga gtttattatg atggcgatac atgggacatg    360

gttaaagatc catctaaaat aactaaagtt cttccaattg caagtatact tactctttca    420

gcaacagggt ctgaaatgga tcaaattgca gtaatttcaa atatggagac taatgaaaag    480

cttggagtag gacatgatga tatgagacct aaattttcag tgttagatcc tacatatact    540

tttacagtac ctaaaaatca aacagcagcg ggaacagctg acattatgag tcacaccttt    600

gaatcttact ttagtggtgt tgaaggtgct tatgtgcagg acggtatagc agaagcaatc    660

ttaagaacat gtataaagta tggaaaaata gcaatggaga agactgatga ttacgaggct    720

agagctaatt tgatgtgggc ttcaagttta gctataaatg gtctattatc acttggtaag    780

gatagaaaat ggagttgtca tcctatggaa cacgagttaa gtgcatatta tgatataaca    840

catggtgtag gacttgcaat tttaacacct aattggatgg aatatattct aaatgacgat    900

acacttcata aatttgtttc ttatggaata aatgtttggg gaatagacaa gaacaaagat    960

aactatgaaa tagcacgaga ggctattaaa aatacgagag aatactttaa ttcattgggt   1020

attccttcaa agcttagaga agttggaata ggaaaagata aactagaact aatggcaaag   1080

caagctgtta gaaattctgg aggaacaata ggaagtttaa gaccaataaa tgcagaggat   1140

gttcttgaga tatttaaaaa atcttattaa                                    1170
```

```
<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190
```

```
Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385
```

<210> SEQ ID NO 17
<211> LENGTH: 780
<212> TYPE: DNA
<213> ORGANISM: Klebsiella pneumoniae

<400> SEQUENCE: 17

```
atgaatcatt ctgctgaatg cacctgcgaa gagagtctat gcgaaaccct gcgggcgttt     60

tccgcgcagc atcccgagag cgtgctctat cagacatcgc tcatgagcgc cctgctgagc    120

ggggtttacg aaggcagcac caccatcgcg gacctgctga aacacggcga tttcggcctc    180

ggcaccttta atgagctgga cggggagctg atcgccttca gcagtcaggt ctatcagctg    240

cgcgccgacg gcagcgcgcg caaagcccag ccggagcaga aaacgccgtt cgcggtgatg    300

acctggttcc agccgcagta ccggaaaacc tttgaccatc cggtgagccg ccagcagctg    360

cacgaggtga tcgaccagca aatcccctct gacaacctgt tctgcgccct gcgcatcgac    420

ggccatttcc gccatgccca tacccgcacc gtgccgcgcc agacgccgcc gtaccgggcg    480

atgaccgacg tcctcgacga tcagccggtg ttccgcttta accagcgcga aggggtgctg    540

gtcggcttcc ggaccccgca gcatatgcag gggatcaacg tcgccgggta tcacgagcac    600

tttattaccg atgaccgcaa aggcggcggt cacctgctgg attaccagct cgaccatggg    660

gtgctgacct tcggcgaaat tcacaagctg atgatcgacc tgcccgccga cagcgcgttc    720

ctgcaggcta atctgcatcc cgataatctc gatgccgcca tccgttccgt agaaagttaa    780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag     60

ctggaagctc agggagtacg ccaggtgttc ggcatccccg gcgccaaaat tgacaaggtc    120

ttcgactcac tgctggattc ctcgattcgc attattccgg tacgccacga agccaacgcc    180

gcgtttatgg ccgccgccgt cggacgcatt accggcaaag cgggcgtggc gctggtcacc    240

tccggtccgg gctgttccaa cctgatcacc ggcatggcca ccgcgaacag cgaaggcgac    300

ccggtggtgg ccctgggcgg cgcggtaaaa cgcgccgata aagcgaagca ggtccaccag    360

agtatggata cggtggcgat gttcagcccg gtcaccaaat acgccgtcga ggtgacggcg    420

ccggatgcgc tggcggaagt ggtctccaac gccttccgcg ccgccgagca gggccggccg    480

ggcagcgcgt tcgttagcct gccgcaggat gtggtcgatg gcccggtcag cggcaaagtg    540
```

-continued

```
ctgccggcca gcggggcccc gcagatgggc gccgcgccgg atgatgccat cgaccaggtg    600

gcgaagctta tcgcccaggc gaagaacccg atcttcctgc tcggcctgat ggccagccag    660

ccggaaaaca gcaaggcgct gcgccgtttg ctggagacca gccatattcc agtcaccagc    720

acctatcagg ccgccggagc ggtgaatcag gataacttct ctcgcttcgc cggccgggtt    780

gggctgttta acaaccaggc cggggaccgt ctgctgcagc tcgccgacct ggtgatctgc    840

atcggctaca gcccggtgga atacgaaccg gcgatgtgga acagcggcaa cgcgacgctg    900

gtgcacatcg acgtgctgcc cgcctatgaa gagcgcaact acaccccgga tgtcgagctg    960

gtgggcgata tcgccggcac tctcaacaag ctggcgcaaa atatcgatca tcggctggtg   1020

ctctccccgc aggcggcgga gatcctccgc gaccgccagc accagcgcga gctgctggac   1080

cgccgcggcg cgcagctgaa ccagtttgcc ctgcatccgc tgcgcatcgt tcgcgccatg   1140

caggacatcg tcaacagcga cgtcacgttg accgtggaca tgggcagctt ccatatctgg   1200

attgcccgct acctgtacag cttccgcgcc cgtcaggtga tgatctccaa cggccagcag   1260

accatgggcg tcgccctgcc ctgggctatc ggcgcctggc tggtcaatcc tgagcgaaaa   1320

gtggtctccg tctccggcga cggcggcttc ctgcagtcga gcatggagct ggagaccgcc   1380

gtccgcctga aagccaacgt actgcacctg atctgggtcg ataacggcta caacatggtg   1440

gccattcagg aagagaaaaa ataccagcgc ctgtccggcg tcgagttcgg gccgatggat   1500

tttaaagcct atgccgaatc cttcggcgcg aaagggtttg ccgtggaaag cgccgaggcg   1560

ctggagccga ccctgcacgc ggcgatggac gtcgacggcc cggcggtggt ggccattccg   1620

gtggattatc gcgataaccc gctgctgatg ggccagctgc atctgagtca gattctgtaa   1680
```

```
<210> SEQ ID NO 20
<211> LENGTH: 559
<212> TYPE: PRT
<213> ORGANISM: Klebsiella pneumoniae

<400> SEQUENCE: 20

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175
```

-continued

```
Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555
```

<210> SEQ ID NO 21
<211> LENGTH: 771
<212> TYPE: DNA
<213> ORGANISM: Klebsiella pneumoniae

<400> SEQUENCE: 21

```
atgaaaaaag tcgcacttgt taccggcgcc ggccagggga ttggtaaagc tatcgccctt     60

cgtctggtga aggatggatt tgccgtggcc attgccgatt ataacgacgc caccgccaaa    120

gcggtcgcct cggaaatcaa ccaggccggc ggacacgccg tggcggtgaa agtggatgtc    180

tccgaccgcg atcaggtatt tgccgccgtt gaacaggcgc gcaaaacgct gggcggcttc    240

gacgtcatcg tcaataacgc cggtgtggca ccgtctacgc cgatcgagtc cattaccccg    300

gagattgtcg acaaagtcta caacatcaac gtcaaagggg tgatctgggg tattcaggcg    360

gcggtcgagg cctttaagaa agaggggcac ggcgggaaaa tcatcaacgc ctgttcccag    420

gccggccacg tcggcaaccc ggagctggcg gtgtatagct ccagtaaatt cgcggtacgc    480

ggcttaaccc agaccgccgc tcgcgacctc gcgccgctgg gcatcacggt caacggctac    540

tgcccgggga ttgtcaaaac gccaatgtgg gccgaaattg accgccaggt gtccgaagcc    600

gccggtaaac cgctgggcta cggtaccgcc gagttcgcca aacgcatcac tctcggtcgt    660

ctgtccgagc cggaagatgt cgccgcctgc gtctcctatc ttgccagccc ggattctgat    720

tacatgaccg gtcagtcgtt gctgatcgac ggcgggatgg tatttaacta a             771
```

```
<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240
```

```
Tyr Met Thr Gly Gln Ser Leu Leu Ile Asp Gly Gly Met Val Phe Asn
              245                 250                 255
```

<210> SEQ ID NO 23
<211> LENGTH: 1665
<212> TYPE: DNA
<213> ORGANISM: Klebsiella oxytoca

<400> SEQUENCE: 23

```
atgagatcga aaagatttga agcactggcg aaacgccctg tgaatcagga cggcttcgtt      60

aaggagtgga tcgaagaagg ctttatcgcg atggaaagcc cgaacgaccc aaaaccgtcg     120

attaaaatcg ttaacggcgc ggtgaccgag ctggacggga aaccggtaag cgattttgac     180

ctgatcgacc actttatcgc ccgctacggt atcaacctga accgcgccga agaagtgatg     240

gcgatggatt cggtcaagct ggccaacatg ctgtgcgatc cgaacgttaa acgcagcgaa     300

atcgtcccgc tgaccaccgc gatgacgccg gcgaaaattg tcgaagtggt ttcgcatatg     360

aacgtcgtcg agatgatgat ggcgatgcag aaaatgcgcg cccgccgcac cccgtcccag     420

caggcgcacg tcaccaacgt caaagataac ccggtacaga ttgccgccga cgccgccgaa     480

ggggcatggc gcggatttga cgaacaggaa accaccgttg cggtagcgcg ctatgcgccg     540

ttcaacgcca tcgcgctgct ggtgggctcg caggtaggcc gtccgggcgt gctgacgcag     600

tgctcgctgg aagaagccac cgagctgaag ctcggcatgc tgggccacac ctgctacgcc     660

gaaaccatct ccgtctacgg caccgagccg gtctttaccg acggcgacga cacgccgtgg     720

tcgaagggct tcctcgcctc gtcctacgcc tctcgcgggc tgaaaatgcg ctttacctcc     780

ggctccggct cggaagtgca gatgggctac gccgaaggca aatccatgct ttatctggaa     840

gcgcgctgca tctacatcac caaagccgcg ggcgtacagg gtctgcaaaa cggttccgta     900

agctgcatcg gcgtgccgtc tgcggtgcct tccggcattc gcgcggtgct ggcggaaaac     960

ctgatctgtt cgtcgctgga tctggagtgc gcctccagca acgaccagac cttcacccac    1020

tccgatatgc gtcgtaccgc gcgcctgctg atgcagttcc tgccgggcac cgactttatc    1080

tcctccggtt attccgcggt gccgaactac gacaacatgt tcgccggctc caacgaagat    1140

gccgaagact ttgacgacta caacgtcatc cagcgcgacc tgaaggtgga cggcggtttg    1200

cgtccggttc gcgaagagga cgtcatcgcc atccgtaaca aagccgcccg cgcgctgcag    1260

gccgtgtttg ccggaatggg gctgccgccg attaccgatg aagaagttga agccgcgacc    1320

tacgcccacg gttcgaaaga tatgccggag cgcaacatcg tcgaagacat caagttcgcc    1380

caggaaatca tcaataaaaa ccgcaacggt ctggaagtgg tgaaagcgct ggcgcagggc    1440

ggattcaccg acgtggccca ggacatgctc aacatccaga aagctaagct gaccggggac    1500

tacctgcata cctccgcgat tatcgtcggc gacgggcagg tgctgtcagc cgtcaacgac    1560

gtcaacgact atgccggtcc ggcaacgggc tatcgcctgc agggcgaacg ctgggaagag    1620

attaaaaaca tccctggcgc tcttgatccc aacgagattg attaa                    1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15
```

-continued

```
Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
```

```
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550


<210> SEQ ID NO 25
<211> LENGTH: 675
<212> TYPE: DNA
<213> ORGANISM: Klebsiella oxytoca

<400> SEQUENCE: 25

atggaaatta atgaaaaatt gctgcgccag ataattgaag acgtgctcag cgagatgaag      60

ggcagcgata aaccggtctc gtttaatgcg ccggcggcct ccgcggcgcc ccaggccacg     120

ccgcccgccg gcgacggctt cctgacggaa gtgggcgaag cgcgtcaggg aacccagcag     180

gacgaagtga ttatcgccgt cggcccggct ttcggcctgg cgcagaccgt caatatcgtc     240

ggcatcccgc ataagagcat tttgcgcgaa gtcattgccg gtattgaaga agaaggcatt     300

aaggcgcgcg tgattcgctg ctttaaatcc tccgacgtgg ccttcgtcgc cgttgaaggt     360

aatcgcctga gcggctccgg catctctatc ggcatccagt cgaaaggcac cacggtgatc     420

caccagcagg ggctgccgcc gctctctaac ctggagctgt tcccgcaggc gccgctgctg     480

accctggaaa cctatcgcca gatcggcaaa aacgccgccc gctatgcgaa acgcgaatcg     540

ccgcagccgg tcccgacgct gaatgaccag atggcgcggc cgaagtacca ggcgaaatcg     600

gccattttgc acattaaaga gaccaagtac gtggtgacgg gcaaaaaccc gcaggaactg     660

cgcgtggcgc tttga                                                      675


<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
```

-continued

```
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220


<210> SEQ ID NO 27
<211> LENGTH: 522
<212> TYPE: DNA
<213> ORGANISM: Klebsiella oxytoca

<400> SEQUENCE: 27

atgaataccg acgcaattga atcgatggta cgcgacgtat tgagccgcat gaacagcctg      60

cagggcgagg cgcctgcggc ggctccggcg gctggcggcg cgtcccgtag cgccagggtc     120

agcgactacc cgctggcgaa caagcacccg gaatgggtga aaaccgccac caataaaacg     180

ctggacgact ttacgctgga aaacgtgctg agcaataaag tcaccgccca ggatatgcgt     240

attaccccgg aaaccctgcg cttacaggct tctattgcca aagacgcggg ccgcgaccgg     300

ctggcgatga acttcgagcg cgccgccgag ctgaccgcgg taccggacga tcgcattctt     360

gaaatctaca acgccctccg cccctatcgc tcgacgaaag aggagctgct ggcgatcgcc     420

gacgatctcg aaagccgcta tcaggcgaag atttgcgccg ctttcgttcg cgaagcggcc     480

acgctgtacg tcgagcgtaa aaaactcaaa ggcgacgatt aa                        522


<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
```

-continued

```
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170


<210> SEQ ID NO 29
<211> LENGTH: 1041
<212> TYPE: DNA
<213> ORGANISM: Rhodococcus ruber

<400> SEQUENCE: 29

atgaaagccc tccagtacac cgagatcggc tccgagccgg tcgtcgtcga cgtccccacc      60

ccggcgcccg ggccgggtga gatcctgctg aaggtcaccg cggccggctt gtgccactcg     120

gacatcttcg tgatggacat gccggcagag cagtacatct acggtcttcc cctcaccctc     180

ggccacgagg gcgtcggcac cgtcgccgaa ctcggcgccg gcgtcaccgg attcgagacg     240

ggggacgccg tcgccgtgta cgggccgtgg gggtgcggtg cgtgccacgc gtgcgcgcgc     300

ggccgggaga actactgcac ccgcgccgcc gagctgggca tcacccccgcc cggtctcggc     360

tcgcccgggt cgatggccga gtacatgatc gtcgactcgg cgcgccacct cgtcccgatc     420

ggggacctcg accccgtcgc ggcggttccg ctcaccgacg cgggcctgac gccgtaccac     480

gcgatctcgc gggtcctgcc cctgctggga cccggctcga ccgcggtcgt catcggggtc     540

ggcggactcg ggcacgtcgg catccagatc ctgcgcgccg tcagcgcggc ccgcgtgatc     600

gccgtcgatc tcgacgacga ccgactcgcg ctcgcccgcg aggtcggcgc cgacgcggcg     660

gtgaagtcgg gcgccggggc ggcggacgcg atccgggagc tgaccggcgg tgagggcgcg     720

acggcggtgt tcgacttcgt cggcgcccag tcgacgatcg acacggcgca gcaggtggtc     780

gcgatcgacg ggcacatctc ggtggtcggc atccatgccg gcgcccacgc caaggtcggc     840

ttcttcatga tcccgttcgg cgcgtccgtc gtgacgccgt actggggcac gcggtccgag     900

ctgatggacg tcgtggacct ggcccgtgcc ggccggctcg acatccacac cgagacgttc     960

accctcgacg agggacccac ggcctaccgg cggctacgcg agggcagcat ccgcggccgc    1020

ggggtggtcg tcccgggctg a                                              1041


<210> SEQ ID NO 30
<211> LENGTH: 346
<212> TYPE: PRT
<213> ORGANISM: Rhodococcus ruber

<400> SEQUENCE: 30

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
```

-continued

```
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345
```

<210> SEQ ID NO 31
<211> LENGTH: 1476
<212> TYPE: DNA
<213> ORGANISM: Escherichia coli

<400> SEQUENCE: 31

```
atggctaact acttcaatac actgaatctg cgccagcagc tggcacagct gggcaaatgt     60

cgctttatgg gccgcgatga attcgccgat ggcgcgagct accttcaggg taaaaaagta    120

gtcatcgtcg gctgtggcgc acagggtctg aaccagggcc tgaacatgcg tgattctggt    180

ctcgatatct cctacgctct gcgtaaagaa gcgattgccg agaagcgcgc gtcctggcgt    240

aaagcgaccg aaaatggttt taaagtgggt acttacgaag aactgatccc acaggcggat    300

ctggtgatta acctgacgcc ggacaagcag cactctgatg tagtgcgcac cgtacagcca    360

ctgatgaaag acggcgcggc gctgggctac tcgcacggtt tcaacatcgt cgaagtgggc    420

gagcagatcc gtaaagatat caccgtagtg atggttgcgc cgaaatgccc aggcaccgaa    480

gtgcgtgaag agtacaaacg tgggttcggc gtaccgacgc tgattgccgt tcacccggaa    540
```

-continued

```
aacgatccga aaggcgaagg catggcgatt gccaaagcct gggcggctgc aaccggtggt    600

caccgtgcgg gtgtgctgga atcgtccttc gttgcggaag tgaaatctga cctgatgggc    660

gagcaaacca tcctgtgcgg tatgttgcag gctggctctc tgctgtgctt cgacaagctg    720

gtggaagaag gtaccgatcc agcatacgca gaaaaactga ttcagttcgg ttgggaaacc    780

atcaccgaag cactgaaaca gggcggcatc accctgatga tggaccgtct ctctaacccg    840

gcgaaactgc gtgcttatgc gctttctgaa cagctgaaag agatcatggc acccctgttc    900

cagaaacata tggacgacat catctccggc gaattctctt ccggtatgat ggcggactgg    960

gccaacgatg ataagaaact gctgacctgg cgtgaagaga ccggcaaaac cgcgtttgaa   1020

accgcgccgc agtatgaagg caaaatcggc gagcaggagt acttcgataa aggcgtactg   1080

atgattgcga tggtgaaagc gggcgttgaa ctggcgttcg aaaccatggt cgattccggc   1140

atcattgaag agtctgcata ttatgaatca ctgcacgagc tgccgctgat tgccaacacc   1200

atcgcccgta agcgtctgta cgaaatgaac gtggttatct ctgataccgc tgagtacggt   1260

aactatctgt tctcttacgc ttgtgtgccg ttgctgaaac cgtttatggc agagctgcaa   1320

ccgggcgacc tgggtaaagc tattccggaa ggcgcggtag ataacgggca actgcgtgat   1380

gtgaacgaag cgattcgcag ccatgcgatt gagcaggtag gtaagaaact gcgcggctat   1440

atgacagata tgaaacgtat tgctgttgcg ggttaa                             1476


<210> SEQ ID NO 32
<211> LENGTH: 491
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205
```

-continued

```
Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490


<210> SEQ ID NO 33
<211> LENGTH: 1851
<212> TYPE: DNA
<213> ORGANISM: Escherichia coli

<400> SEQUENCE: 33

atgcctaagt accgttccgc caccaccact catggtcgta atatggcggg tgctcgtgcg      60

ctgtggcgcg ccaccggaat gaccgacgcc gatttcggta agccgattat cgcggttgtg     120

aactcgttca cccaatttgt accgggtcac gtccatctgc gcgatctcgg taaactggtc     180

gccgaacaaa ttgaagcggc tggcggcgtt gccaaagagt tcaacaccat tgcggtggat     240

gatgggattg ccatgggcca cgggggggatg ctttattcac tgccatctcg cgaactgatc     300

gctgattccg ttgagtatat ggtcaacgcc cactgcgccg acgccatggt ctgcatctct     360

aactgcgaca aaatcacccc ggggatgctg atggcttccc tgcgcctgaa tattccggtg     420

atctttgttt ccggcggccc gatggaggcc gggaaaacca aactttccga tcagatcatc     480

aagctcgatc tggttgatgc gatgatccag ggcgcagacc cgaaagtatc tgactcccag     540
```

```
agcgatcagg ttgaacgttc cgcgtgtccg acctgcggtt cctgctccgg gatgtttacc    600

gctaactcaa tgaactgcct gaccgaagcg ctgggcctgt cgcagccggg caacggctcg    660

ctgctggcaa cccacgccga ccgtaagcag ctgttcctta atgctggtaa acgcattgtt    720

gaattgacca aacgttatta cgagcaaaac gacgaaagtg cactgccgcg taatatcgcc    780

agtaaggcgg cgtttgaaaa cgccatgacg ctggatatcg cgatgggtgg atcgactaac    840

accgtacttc acctgctggc ggcggcgcag gaagcggaaa tcgacttcac catgagtgat    900

atcgataagc tttcccgcaa ggttccacag ctgtgtaaag ttgcgccgag cacccagaaa    960

taccatatgg aagatgttca ccgtgctggt ggtgttatcg gtattctcgg cgaactggat   1020

cgcgcggggt tactgaaccg tgatgtgaaa aacgtacttg gcctgacgtt gccgcaaacg   1080

ctggaacaat acgacgttat gctgacccag gatgacgcgg taaaaaatat gttccgcgca   1140

ggtcctgcag gcattcgtac cacacaggca ttctcgcaag attgccgttg ggatacgctg   1200

gacgacgatc gcgccaatgg ctgtatccgc tcgctggaac acgcctacag caaagacggc   1260

ggcctggcgg tgctctacgg taactttgcg gaaaacggct gcatcgtgaa aacggcaggc   1320

gtcgatgaca gcatcctcaa attcaccggc ccggcgaaag tgtacgaaag ccaggacgat   1380

gcggtagaag cgattctcgg cggtaaagtt gtcgccggag atgtggtagt aattcgctat   1440

gaaggcccga aaggcggtcc ggggatgcag gaaatgctct acccaaccag cttcctgaaa   1500

tcaatgggtc tcggcaaagc ctgtgcgctg atcaccgacg gtcgtttctc tggtggcacc   1560

tctggtcttt ccatcggcca cgtctcaccg gaagcggcaa gcggcggcag cattggcctg   1620

attgaagatg gtgacctgat cgctatcgac atcccgaacc gtggcattca gttacaggta   1680

agcgatgccg aactggcggc gcgtcgtgaa gcgcaggacg ctcgaggtga caaagcctgg   1740

acgccgaaaa atcgtgaacg tcaggtctcc tttgccctgc gtgcttatgc cagcctggca   1800

accagcgccg acaaaggcgc ggtgcgcgat aaatcgaaac tgggggggtta a           1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140
```

-continued

```
Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560
```

```
Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615


<210> SEQ ID NO 35
<211> LENGTH: 1662
<212> TYPE: DNA
<213> ORGANISM: Lactococcus lactis

<400> SEQUENCE: 35

tctagacata tgtatactgt gggggattac ctgctggatc gcctgcacga actggggatt      60

gaagaaattt tcggtgtgcc aggcgattat aacctgcagt tcctggacca gattatctcg     120

cacaaagata tgaagtgggt cggtaacgcc aacgaactga acgcgagcta tatggcagat     180

ggttatgccc gtaccaaaaa agctgctgcg tttctgacga cctttggcgt tggcgaactg     240

agcgccgtca acggactggc aggaagctac gccgagaacc tgccagttgt cgaaattgtt     300

gggtcgccta cttctaaggt tcagaatgaa ggcaaatttg tgcaccatac tctggctgat     360

ggggatttta aacattttat gaaaatgcat gaaccggtta ctgcggcccg cacgctgctg     420

acagcagaga atgctacggt tgagatcgac cgcgtcctgt ctgcgctgct gaaagagcgc     480

aagccggtat atatcaatct gcctgtcgat gttgccgcag cgaaagccga aaagccgtcg     540

ctgccactga aaaaagaaaa cagcacctcc aatacatcgg accaggaaat tctgaataaa     600

atccaggaat cactgaagaa tgcgaagaaa ccgatcgtca tcaccggaca tgagatcatc     660

tcttttggcc tggaaaaaac ggtcacgcag ttcatttcta agaccaaact gcctatcacc     720

accctgaact tcggcaaatc tagcgtcgat gaagcgctgc cgagttttct gggtatctat     780

aatggtaccc tgtccgaacc gaacctgaaa gaattcgtcg aaagcgcgga ctttatcctg     840

atgctgggcg tgaaactgac ggatagctcc acaggcgcat ttacccacca tctgaacgag     900

aataaaatga tttccctgaa tatcgacgaa ggcaaaatct ttaacgagcg catccagaac     960

ttcgattttg aatctctgat tagttcgctg ctggatctgt ccgaaattga gtataaaggt    1020

aaatatattg ataaaaaaca ggaggatttt gtgccgtcta atgcgctgct gagtcaggat    1080

cgtctgtggc aagccgtaga aaacctgaca cagtctaatg aaacgattgt tgcggaacag    1140

ggaacttcat ttttcggcgc ctcatccatt tttctgaaat ccaaaagcca tttcattggc    1200

caaccgctgt gggggagtat tggttatacc tttccggcgg cgctgggttc acagattgca    1260

gataaggaat cacgccatct gctgtttatt ggtgacggca gcctgcagct gactgtccag    1320

gaactggggc tggcgatccg tgaaaaaatc aatccgattt gctttatcat caataacgac    1380

ggctacaccg tcgaacgcga aattcatgga ccgaatcaaa gttacaatga catcccgatg    1440

tggaactata gcaaactgcc ggaatccttt ggcgcgacag aggatcgcgt ggtgagtaaa    1500

attgtgcgta cggaaaacga atttgtgtcg gttatgaaag aagcgcaggc tgacccgaat    1560

cgcatgtatt ggattgaact gatcctggca aaagaaggcg caccgaaagt tctgaaaaag    1620

atggggaaac tgtttgcgga gcaaaataaa agctaaggat cc                       1662


<210> SEQ ID NO 36
<211> LENGTH: 548
```

-continued

<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400
```

-continued

```
Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

```
<210> SEQ ID NO 37
<211> LENGTH: 1164
<212> TYPE: DNA
<213> ORGANISM: Escherichia coli

<400> SEQUENCE: 37

atgaacaact ttaatctgca caccccaacc cgcattctgt ttggtaaagg cgcaatcgct      60

ggtttacgcg aacaaattcc tcacgatgct cgcgtattga ttacctacgg cggcggcagc     120

gtgaaaaaaa ccggcgttct cgatcaagtt ctggatgccc tgaaaggcat ggacgtgctg     180

gaatttggcg gtattgagcc aaacccggct tatgaaacgc tgatgaacgc cgtgaaactg     240

gttcgcgaac agaaagtgac tttcctgctg gcggttggcg gcggttctgt actggacggc     300

accaaattta tcgccgcagc ggctaactat ccggaaaata tcgatccgtg gcacattctg     360

caaacgggcg gtaaagagat taaaagcgcc atcccgatgg gctgtgtgct gacgctgcca     420

gcaaccggtt cagaatccaa cgcaggcgcg gtgatctccc gtaaaaccac aggcgacaag     480

caggcgttcc attctgccca tgttcagccg gtatttgccg tgctcgatcc ggtttatacc     540

tacaccctgc cgccgcgtca ggtggctaac ggcgtagtgg acgcctttgt acacaccgtg     600

gaacagtatg ttaccaaacc ggttgatgcc aaaattcagg accgtttcgc agaaggcatt     660

ttgctgacgc taatcgaaga tggtccgaaa gccctgaaag agccagaaaa ctacgatgtg     720

cgcgccaacg tcatgtgggc ggcgactcag gcgctgaacg gtttgattgg cgctggcgta     780

ccgcaggact gggcaacgca tatgctgggc cacgaactga ctgcgatgca cggtctggat     840

cacgcgcaaa cactggctat cgtcctgcct gcactgtgga atgaaaaacg cgataccaag     900

cgcgctaagc tgctgcaata tgctgaacgc gtctggaaca tcactgaagg ttccgatgat     960

gagcgtattg acgccgcgat tgccgcaacc cgcaatttct ttgagcaatt aggcgtgccg    1020

acccacctct ccgactacgg tctggacggc agctccatcc cggctttgct gaaaaaactg    1080

gaagagcacg gcatgaccca actgggcgaa aatcatgaca ttacgttgga tgtcagccgc    1140

cgtatatacg aagccgcccg ctaa                                           1164
```

-continued

```
<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380
```

Ala Ala Arg
385

<210> SEQ ID NO 39
<211> LENGTH: 19
<212> TYPE: DNA
<213> ORGANISM: Artificial
<220> FEATURE:
<223> OTHER INFORMATION: Primer

<400> SEQUENCE: 39
gagtttgatc ctggctcag 19

<210> SEQ ID NO 40
<211> LENGTH: 16
<212> TYPE: DNA
<213> ORGANISM: Artificial
<220> FEATURE:
<223> OTHER INFORMATION: Primer

<400> SEQUENCE: 40
taccttgtta cgactt 16

<210> SEQ ID NO 41
<211> LENGTH: 1468
<212> TYPE: DNA
<213> ORGANISM: Lactobacillus plantarum

<400> SEQUENCE: 41
tctgtcacct taggcggctg gttcctaaaa ggttacccca ccgactttgg gtgttacaaa 60
ctctcatggt gtgacgggcg gtgtgtacaa ggcccgggaa cgtattcacc gcggcatgct 120
gatccgcgat tactagcgat tccgacttca tgtaggcgag ttgcagccta caatccgaac 180
tgagaatggc tttaagagat tagcttactc tcgcgagttc gcaactcgtt gtaccatcca 240
ttgtagcacg tgtgtagccc aggtcataag gggcatgatg atttgacgtc atccccacct 300
tcctccggtt tgtcaccggc agtctcacca gagtgcccaa cttaatgctg gcaactgata 360
ataagggttg cgctcgttgc gggacttaac ccaacatctc acgacacgag ctgacgacaa 420
ccatgcacca cctgtatcca tgtccccgaa gggaacgtct aatctcttag atttgcatag 480
tatgtcaaga cctggtaagg ttcttcgcgt agcttcgaat taaaccacat gctccaccgc 540
ttgtgcgggc ccccgtcaat tcctttgagt ttcagccttg cggccgtact ccccaggcgg 600
aatgcttaat gcgttagctg cagcactgaa gggcggaaac cctccaacac ttagcattca 660
tcgtttacgg tatggactac cagggtatct aatcctgttt gctacccata ctttcgagcc 720
tcagcgtcag ttacagacca gacagccgcc ttcgccactg gtgttcttcc atatatctac 780
gcatttcacc gctacacatg gagttccact gtcctcttct gcactcaagt ttcccagttt 840
ccgatgcact tcttcggttg agccgaaggc tttcacatca gacttaaaaa accgcctgcg 900
ctcgctttac gcccaataaa tccggacaac gcttgccact acgtattacc gcggctgctg 960
gcacgtagtt agccgtggct ttctggttaa ataccgtcaa tacctgaaca gttactctca 1020
gatatgttct tctttaacaa cagagtttta cgagccgaaa cccttcttca ctcacgcggc 1080
gttgctccat cagactttcg tccattgtgg aagattccct actgctgcct cccgtaggag 1140
tttgggccgt gtctcagtcc caatgtggcc gattaccctc tcaggtcggc tacgtatcat 1200
tgccatggtg agccgttacc ccaccatcta gctaatacgc cgcgggacca tccaaaagtg 1260
atagccgaag ccatctttca aactcggacc atgcggtcca agttgttatg cggtattagc 1320

-continued

```
atctgtttcc aggtgttatc ccccgcttct gggcaggttt cccacgtgtt actcaccagt   1380

tcgccactca ctcaaatgta aatcatgatg caagcaccaa tcaataccag agttcgttcg   1440

acttgcatga taggcacgcc gccaggtg                                       1468
```

<210> SEQ ID NO 42
<211> LENGTH: 1469
<212> TYPE: DNA
<213> ORGANISM: Lactobacillus plantarum

<400> SEQUENCE: 42

```
tctgtcccct taggcggctg gttcctaaaa ggttacccca ccgactttgg gtgttacaaa     60

ctctcatggt gtgacgggcg gtgtgtacaa ggcccgggaa cgtattcacc gcggcatgct    120

gatccgcgat tactagcgat tccgacttca tgtaggcgag ttgcagccta caatccgaac    180

tgagaatggc tttaagagat tagcttactc tcgcgagttc gcaactcgtt gtaccatcca    240

ttgtagcacg tgtgtagccc aggtcataag gggcatgatg atttgacgtc atccccacct    300

tcctccggtt tgtcaccggc agtctcacca gagtgcccaa cttaatgctg gcaactgata    360

ataagggttg cgctcgttgc gggacttaac ccaacatctc acgacacgag ctgacgacaa    420

ccatgcacca cctgtatcca tgtccccgaa gggaacgtct aatctcttag atttgcatag    480

tatgtcaaga cctggtaagg ttcttcgcgt agcttcgaat taaaccacat gctccaccgc    540

ttgtgcgggc ccccgtcaat tcctttgagt ttcagccttg cggccgtact ccccaggcgg    600

aatgcttaat gcgttagctg cagcactgaa gggcggaaac cctccaacac ttagcattca    660

tcgtttacgg tatggactac cagggtatct aatcctgttt gctacccata ctttcgagcc    720

tcagcgtcag ttacagacca gacagccgcc ttcgccactg gtgttcttcc atatatctac    780

gcatttcacc gctacacatg gagttccact gtcctcttct gcactcaagt ttcccagttt    840

ccgatgcact tcttcggttg agccgaaggc tttcacatca gacttaaaaa accgcctgcg    900

ctcgctttac gcccaataaa tccggacaac gcttgccacc tacgtattac cgcggctgct    960

ggcacgtagt tagccgtggc tttctggtta aataccgtca atacctgaac agttactctc   1020

agatatgttc ttctttaaca acagagtttt acgagccgaa acccttcttc actcacgcgg   1080

cgttgctcca tcagactttc gtccattgtg gaagattccc tactgctgcc tcccgtagga   1140

gtttgggccg tgtctcagtc ccaatgtggc cgattaccct ctcaggtcgg ctacgtatca   1200

ttgccatggt gagccgttac cccaccatct agctaatacg ccgcgggacc atccaaaagt   1260

gatagccgaa gccatctttc aaactcggac catgcggtcc aagttgttat gcggtattag   1320

catctgtttc caggtgttat cccccgcttc tgggcaggtt tcccacgtgt tactcaccag   1380

ttcgccactc actcaaatgt aaatcatgat gcaagcacca atcaatacca gagttcgttc   1440

gacttgcatg ataggcacgc cgccaggtg                                      1469
```

<210> SEQ ID NO 43
<211> LENGTH: 1450
<212> TYPE: DNA
<213> ORGANISM: Lactobacillus plantarum

<400> SEQUENCE: 43

```
tctgtcccct taggcggctg gttcctaaaa ggttacccca ccgactttgg gtgttacaaa     60

ctctcatggt gtgacgggcg gtgtgtacaa ggcccgggaa cgtattcacc gcggcatgct    120

gatccgcgat tactagcgat tccgacttca tgtaggcgag ttgcagccta caatccgaac    180
```

-continued

```
tgagaatggc tttaagagat tagcttactc tcgcgagttc gcaactcgtt gtaccatcca    240

ttgtagcacg tgtgtagccc aggtcataag gggcatgatg atttgacgtc atccccacct    300

tcctccggtt tgtcaccggc agtctcacca gagtgcccaa cttaatgctg gcaactgata    360

ataagggttg cgctcgttgc gggacttaac ccaacatctc acgacacgag ctgacgacaa    420

ccatgcacca cctgtatcca tgtccccgaa gggaacgtct aatctcttag atttgcatag    480

tatgtcaaga cctggtaagg ttcttcgcgt agcttcgaat taaaccacat gctccaccgc    540

ttgtgcgggc ccccgtcaat tcctttgagt ttcagccttg cggccgtact ccccaggcgg    600

aatgcttaat gcgttagctg cagcactgaa gggcggaaac cctccaacac ttagcattca    660

tcgtttacgg tatggactac cagggtatct aatcctgttt gctacccata ctttcgagcc    720

tcagcgtcag ttacagacca gacagccgcc ttcgccactg gtgttcttcc atatatctac    780

gcatttcacc gctacacatg gagttccact gtcctcttct gcactcaagt ttcccagttt    840

ccgatgcact tcttcggttg agccgaaggc tttcacatca gacttaaaaa accgcctgcg    900

ctcgctttac gcccaataaa tccggacaac gcttgccacc tacgtattac cgcggctgct    960

ggcacgtagt tagccgtggc tttctggtta aataccgtca atacctgaac agttactctc   1020

agatatgttc ttctttaaca acagagtttt acgagccgaa acccttcttc actcacgcgg   1080

cgttgctcca tcagactttc gtccattgtg gaagattccc tactgctgcc tcccgtagga   1140

gtttgggccg tgtctcagtc ccaatgtggc cgattaccct ctcaggtcgg ctacgtatca   1200

ttgccatggt gagccgttac cccaccatct agctaatacg ccgcgggacc atccaaaagt   1260

gatagccgaa gccatctttc aaactcggac catgcggtcc aagttgttat gcggtattag   1320

catctgtttc caggtgttat cccccgcttc tgggcaggtt tcccacgtgt tactcaccag   1380

ttcgccactc actcaaatgt aaatcatgat gcaagcacca atcaatacca gagttcgttc   1440

gacttgcatg                                                          1450
```

<210> SEQ ID NO 44
<211> LENGTH: 1469
<212> TYPE: DNA
<213> ORGANISM: lactobaillus arizonensis

<400> SEQUENCE: 44

```
tctgtccacc ttaggcggct ggttcctaaa aggttacccc accgactttg ggtgttacaa     60

actctcatgg tgtgacgggc ggtgtgtaca aggcccggga acgtattcac cgcggcatgc    120

tgatccgcga ttactagcga ttccgacttc atgtaggcga gttgcagcct acaatccgaa    180

ctgagaatgg ctttaagaga ttagcttact ctcgcgagtt cgcaactcgt tgtaccatcc    240

attgtagcac gtgtgtagcc caggtcataa ggggcatgat gatttgacgt catccccacc    300

ttcctccggt ttgtcaccgg cagtctcacc agagtgccca acttaatgct ggcaactgat    360

aataagggtt gcgctcgttg cgggacttaa cccaacatct cacgacacga gctgacgaca    420

accatgcacc acctgtatcc atgtccccga agggaacgtc taatctctta gatttgcata    480

gtatgtcaag acctggtaag gttcttcgcg tagcttcgaa ttaaaccaca tgctccaccg    540

cttgtgcggg cccccgtcaa ttcctttgag tttcagcctt gcggccgtac tccccaggcg    600

gaatgcttaa tgcgttagct gcagcactga agggcggaaa ccctccaaca cttagcattc    660

atcgtttacg gtatggacta ccagggtatc taatcctgtt tgctacccat actttcgagc    720

ctcagcgtca gttacagacc agacagccgc cttcgccact ggtgttcttc catatatcta    780

cgcatttcac cgctacacat ggagttccac tgtcctcttc tgcactcaag tttcccagtt    840
```

-continued

```
tccgatgcac ttcttcggtt gagccgaagg ctttcacatc agacttaaaa aaccgcctgc    900

gctcgcttta cgcccaataa atccggacaa cgcttgccac ctacgtatta ccgcggctgc    960

tggcacgtag ttagccgtgg ctttctggtt aaataccgtc aatacctgaa cagttactct   1020

cagatatgtt cttctttaac aacagagttt tacgagccga aacccttctt cactcacgcg   1080

gcgttgctcc atcagacttt cgtccattgt ggaagattcc ctactgctgc ctcccgtagg   1140

agtttgggcc gtgtctcagt cccaatgtgg ccgattaccc tctcaggtcg gctacgtatc   1200

attgccatgg tgagccgtta ccccaccatc tagctaatac gccgcgggac catccaaaag   1260

tgatagccga agccatcttt caaactcgga ccatgcggtc caagttgtta tgcggtatta   1320

gcatctgttt ccaggtgtta tcccccgctt ctgggcaggt ttcccacgtg ttactcacca   1380

gttcgccact cactcaaatg taaatcatga tgcaagcacc aatcaatacc agagttcgtt   1440

cgacttgcat gataggcacg ccgccaggt                                     1469
```